(12) United States Patent
Hurtado et al.

(10) Patent No.: US 12,186,072 B2
(45) Date of Patent: Jan. 7, 2025

(54) TECHNIQUES FOR QUANTIFYING RESPIRATION USING A WEARABLE DEVICE AND RELATED SYSTEMS AND METHODS

(71) Applicants: Pontificia Universidad Católica de Chile, Santiago (CL); Fundación Copec Universidad Católica, Santiago (CL)

(72) Inventors: Daniel Hurtado, Santiago (CL); Angel Abusleme, Santiago (CL); Javier Chavez, Octava Region (CL)

(73) Assignees: Pontificia Universidad Católica de Chile, Santiago (CL); Fundación Copec Universidad Católica, Santiago (CL)

( * ) Notice: Subject to any disclaimer, the term of this patent is extended or adjusted under 35 U.S.C. 154(b) by 1054 days.

(21) Appl. No.: 16/960,269

(22) PCT Filed: Jan. 11, 2019

(86) PCT No.: PCT/IB2019/050229
§ 371 (c)(1),
(2) Date: Jul. 6, 2020

(87) PCT Pub. No.: WO2019/138372
PCT Pub. Date: Jul. 18, 2019

(65) Prior Publication Data
US 2021/0106254 A1    Apr. 15, 2021

Related U.S. Application Data

(60) Provisional application No. 62/616,919, filed on Jan. 12, 2018.

(51) Int. Cl.
*A61B 5/08*    (2006.01)
*A61B 5/00*    (2006.01)
*A61B 5/087*    (2006.01)

(52) U.S. Cl.
CPC .......... *A61B 5/0826* (2013.01); *A61B 5/0816* (2013.01); *A61B 5/0878* (2013.01); *A61B 5/682* (2013.01); *A61B 5/6832* (2013.01)

(58) Field of Classification Search
CPC ..... A61B 5/0816; A61B 5/0878; A61B 5/682; A61B 5/6832
See application file for complete search history.

(56) References Cited

U.S. PATENT DOCUMENTS 5,069,222 A    12/1991    McDonald, Jr.
5,190,048 A    3/1993    Wilkinson
(Continued)

FOREIGN PATENT DOCUMENTS

CN    201488821 U    5/2010
CN    101856230 A    10/2010
(Continued)

OTHER PUBLICATIONS

Invitation to Pay Additional Fees in connection with International Application No. PCT/IB2019/050229, mailed May 30, 2019.
(Continued)

*Primary Examiner* — Puya Agahi
(74) *Attorney, Agent, or Firm* — Wolf, Greenfield & Sacks, P.C.

(57) ABSTRACT

Techniques for quantifying respiration using a wearable device are described. According to some aspects, a wearable device includes multiple thermal sensors thermally coupled to one or more heat spreaders. The wearable device may in some cases be small enough to be wearable between the mouth and nose of the patient, such as via an adhesive
(Continued)

attachment to the upper lip. When the patient exhales, air is produced through the mouth and/or through the nose. Each heat spreader may absorb heat of exhaled air which may thermally propagate to a thermal sensor coupled to the heat spreader. By measuring the change in temperature over time measured by the thermal sensors, measures of respiration such as respiratory rate, minute volume and/or tidal volume of the patient may be determined. Such measures may be determined by the wearable device or by an external device to which data is transmitted.

20 Claims, 19 Drawing Sheets

(56) References Cited

U.S. PATENT DOCUMENTS

| | | | |
|---|---|---|---|
| 2003/0028120 | A1 | 2/2003 | Mault et al. |
| 2003/0065274 | A1 | 4/2003 | Mault et al. |
| 2009/0306528 | A1 | 12/2009 | Curti et al. |
| 2010/0268105 | A1 | 10/2010 | Feldman et al. |
| 2012/0150058 | A1* | 6/2012 | Zubrow ............ A61B 5/0826 |
| | | | 600/538 |
| 2015/0351699 | A1 | 12/2015 | Addison et al. |
| 2019/0175064 | A1* | 6/2019 | Haveri ............ A61M 16/0666 |

FOREIGN PATENT DOCUMENTS

| | | |
|---|---|---|
| CN | 201948995 U | 8/2011 |
| CN | 202207144 U | 5/2012 |
| CN | 203480336 U | 3/2014 |
| CN | 103957973 A | 7/2014 |
| CN | 104523276 A | 4/2015 |
| CN | 104661587 A | 5/2015 |
| CN | 105135593 A | 12/2015 |
| CN | 106175772 A | 12/2016 |
| CN | 107405508 A | 11/2017 |
| GB | 2512955 A | 10/2014 |

OTHER PUBLICATIONS

International Search Report and Written Opinion in connection with International Application No. PCT/IB2019/050229, mailed Jul. 19, 2019.
International Preliminary Report on Patentability in connection with International Application No. PCT/IB2019/050229, mailed Jul. 23, 2020.
PCT/IB2019/050229, May 30, 2019, Invitation to Pay Additional Fees.
PCT/IB2019/050229, Jul. 19, 2019, International Search Report and Written Opinion.
PCT/IB2019/050229, Jul. 23, 2020, International Preliminary Report on Patentability.

* cited by examiner

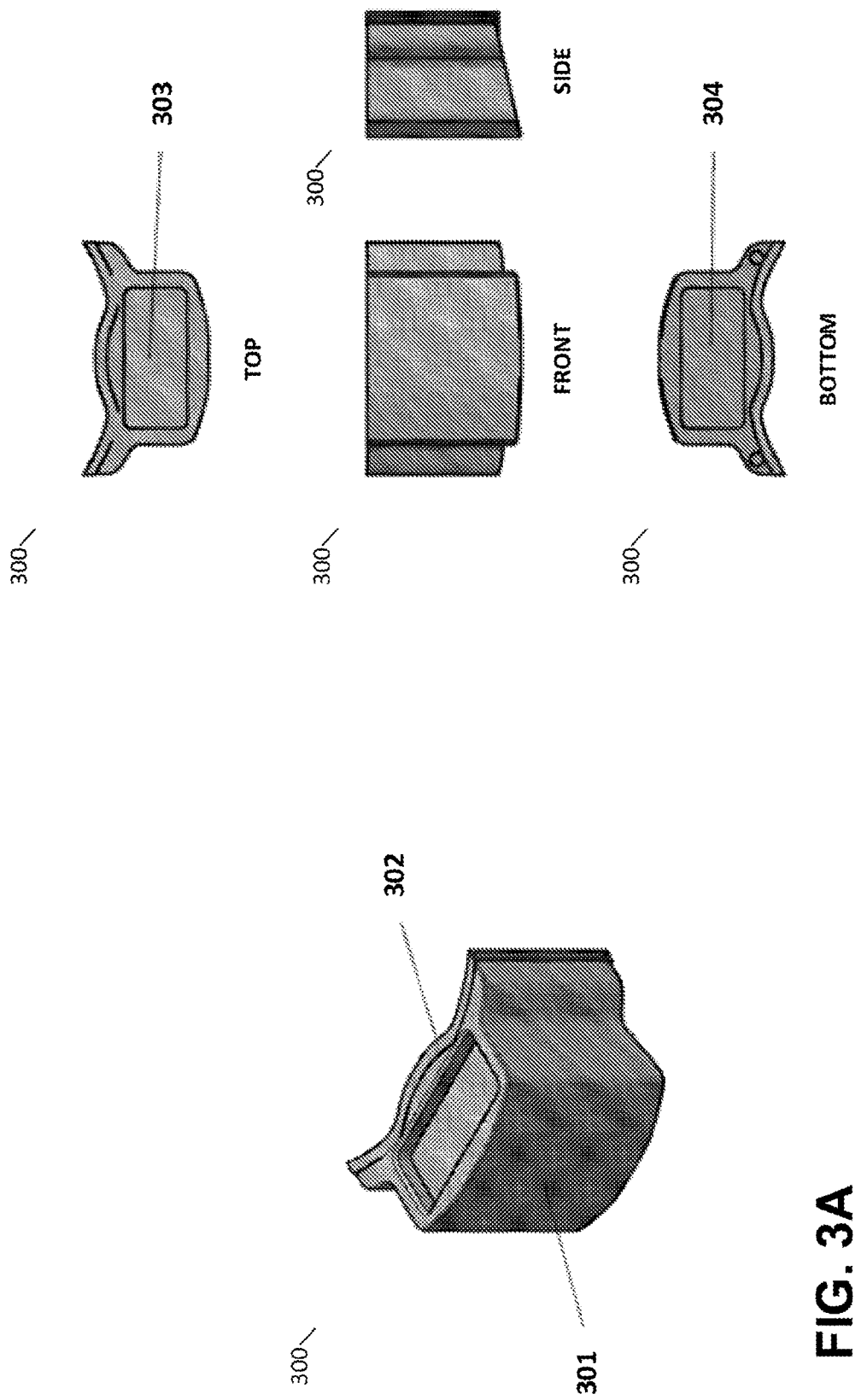

TECHNIQUES FOR QUANTIFYING RESPIRATION USING A WEARABLE DEVICE AND RELATED SYSTEMS AND METHODS

CROSS-REFERENCE TO RELATED APPLICATIONS

This application is a national stage filing under 35 U.S.C. § 371 of International Patent Application Serial No. PCT/IB2019/050229, filed Jan. 11, 2019, which claims priority to U.S. Application Ser. No. 62/616,919, filed Jan. 12, 2018, each of which is herein incorporated by reference in its entirety.

BACKGROUND

Critical respiratory events, during which a subject's breathing is severely inhibited, can cause injury or even death. Common forms of critical respiratory events include respiratory depression, which occurs when a subject has a reduced urge to breathe, and upper-airway obstructions. Respiratory depression can be caused by a medical condition, such as a stroke, and/or by medication. Opioids in particular are a common cause of respiratory depression.

During in-patient surgical procedures, however, patient pain is frequently managed using opioids, which causes a substantial number of patients to suffer respiratory depression. For example, one estimate is that patients in a Post Anesthesia Care Unit have an opioid-induced respiratory depression probability of between 0.8% and 6.9% (Karcz et al, Can. J. Respir. Ther., 2013). Since over 50 million in-patient surgeries are performed every year in the U.S., the costs of respiratory depression are substantial.

Opioid-induced respiratory depression ("OIRD") can lead to severe injury including cardiac and respiratory arrest, brain damage, and if not addressed promptly, death. The majority of respiratory depression events occur within 24 hours of a surgical procedure, and at least 13% of the respiratory depression events occur within 2 hours after discharge from the recovery room to the floor (Lorry et al, Anesthesiology, 2015). OIRD has even been detected in patients within 48 hours after discharge from anesthetic care.

SUMMARY

According to some aspects, a wearable device configured to be worn between a subject's mouth and the subject's nose is provided, the device comprising a first heat spreader, a first temperature sensor thermally coupled to the first heat spreader and configured to produce a first signal indicative of a first temperature, a second heat spreader, a second temperature sensor thermally coupled to the second heat spreader and configured to produce a second signal indicative of a second temperature, and at least one controller coupled to the first temperature sensor and the second temperature sensor, the at least one controller configured to receive the first signal from the first temperature sensor and the second signal from the second temperature sensor, and generate an indication of the subject's respiration based at least in part on the received first signal and the received second signal.

According to some embodiments, at least one of the first heat spreader and the second heat spreader comprises copper.

According to some embodiments, the at least one controller is further configured to determine a respiratory rate of the subject based on the received first signal and the received second signal.

According to some embodiments, the wearable device further comprises at least one display configured to display the determined respiratory rate of the subject.

According to some embodiments, the wearable device further comprises at least one audio device configured to produce an audible indication of the respiratory rate of the subject.

According to some embodiments, the wearable device further comprises at least one display configured to produce a visual indication of the generated indication of the subject's respiration.

According to some embodiments, the wearable device further comprises a housing and a layer of adhesive attached to the housing.

According to some embodiments, the at least one controller includes one or more processors, ASICs and/or FPGAs.

According to some embodiments, the at least one controller includes a processor and the wearable device further includes a computer-readable medium storing instructions that, when executed by the processor, generates the indication of the subject's respiration based at least in part on the received first signal and the received second signal.

According to some embodiments, the wearable device further comprises at least one computer readable medium and the at least one controller is configured to store a plurality of generated indications of the subject's respiration on the at least one computer readable medium.

According to some embodiments, the wearable device further comprises at least one communication device coupled to the at least one controller configured to output the generated indication of the subject's respiration to an external device.

According to some aspects, a method of determining a measure of respiration of a subject is provided, the method comprising generating, by at least one controller of a wearable device worn by a subject between the subject's mouth and the subject's nose, at least one indication of the subject's respiration, wherein the wearable device comprises a first heat spreader, a first temperature sensor thermally coupled to the first heat spreader and configured to produce a first signal indicative of a first temperature, a second heat spreader, a second temperature sensor thermally coupled to the second heat spreader and configured to produce a second signal indicative of a second temperature, and the at least one controller, wherein the at least one controller is coupled to the first temperature sensor and the second temperature sensor, and wherein the at least one controller is configured to generate the indication of the subject's respiration based at least in part on the first signal and the second signal, and determining a respiratory rate, ventilation volume and/or a ventilation volume rate of the subject based at least in part on the at least one indication of the subject's respiration.

According to some embodiments, the at least one controller of the wearable device determines the respiratory rate of the subject based at least in part on the at least one indication of the subject's respiration.

According to some embodiments, the method further comprises transmitting the at least one indication of the subject's respiration to a computing device, and the computing device performs said act of determining the respiratory rate, ventilation volume and/or ventilation volume rate of the subject based at least in part on the at least one indication of the subject's respiration.

According to some aspects, a system is provided comprising a computing device, and a wearable device configured to be worn between a subject's mouth and the subject's nose, the device comprising a first heat spreader, a first temperature sensor thermally coupled to the first heat spreader and configured to produce a first signal indicative of a first temperature, a second heat spreader, a second temperature sensor thermally coupled to the second heat spreader and configured to produce a second signal indicative of a second temperature, at least one controller coupled to the first temperature sensor and the second temperature sensor, the at least one controller configured to receive the first signal from the first temperature sensor and the second signal from the second temperature sensor, and generate an indication of the subject's respiration based at least in part on the received first signal and the received second signal, and a communication device configured to transmit the generated indication of the subject's respiration to the computer device.

According to some embodiments, the computing device is configured to determine a respiratory rate of the subject based at least in part on the at least one indication of the subject's respiration received from the communication device of the wearable device.

According to some embodiments, at least one of the first heat spreader and the second heat spreader comprises copper.

According to some embodiments, the at least one controller is further configured to determine a respiratory rate of the subject based on the received first signal and the received second signal.

According to some embodiments, the wearable device further comprises a housing and a layer of adhesive attached to the housing.

According to some embodiments, the at least one controller includes a processor and the wearable device further includes a computer-readable medium storing instructions that, when executed by the processor, generates the indication of the subject's respiration based at least in part on the received first signal and the received second signal.

According to some embodiments, the wearable device further comprises at least computer readable medium and the at least one controller is configured to store a plurality of generated indications of the subject's respiration on the at least one computer readable medium.

The foregoing apparatus and method embodiments may be implemented with any suitable combination of aspects, features, and acts described above or in further detail below. These and other aspects, embodiments, and features of the present teachings can be more fully understood from the following description in conjunction with the accompanying drawings.

BRIEF DESCRIPTION OF DRAWINGS

Various aspects and embodiments will be described with reference to the following figures. It should be appreciated that the figures are not necessarily drawn to scale. In the drawings, each identical or nearly identical component that is illustrated in various figures is represented by a like numeral. For purposes of clarity, not every component may be labeled in every drawing.

FIGS. 3A-3E depict an illustrative design for a wearable device, according to some embodiments;

DETAILED DESCRIPTION

Figure 1:
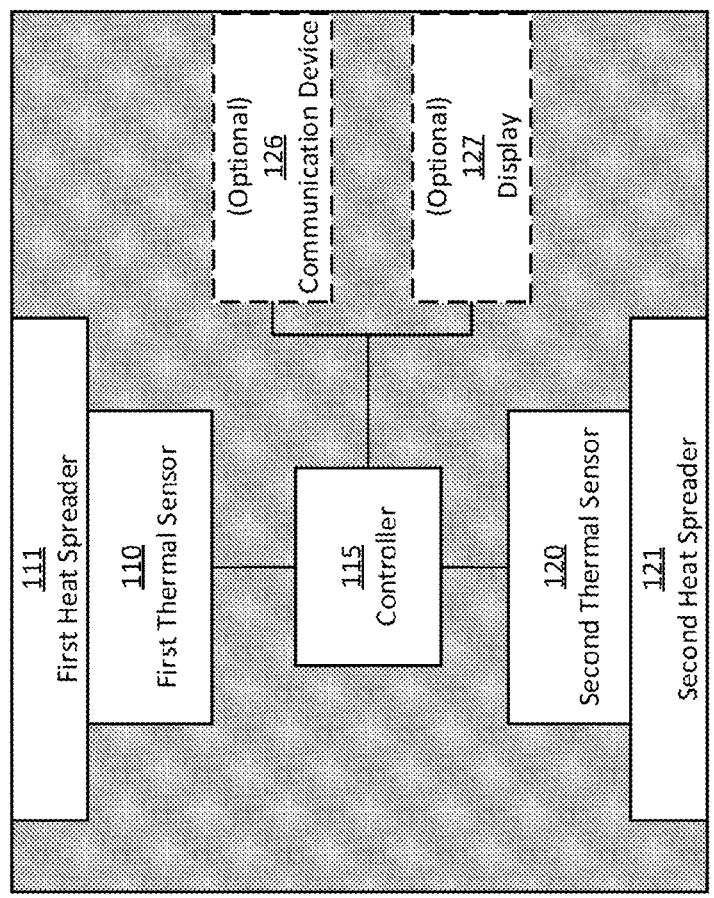
FIG. 1 depicts an illustrative wearable device, according to some embodiments.

The inventors have recognized and appreciated techniques for monitoring patient respiration using a device that is non-invasive, easy to install and use, and offers reliable, early detection of critical respiratory events, including respiratory depression. As discussed above, detection of critical respiratory events may mitigate injuries and monetary costs caused by unnoticed respiratory events. As such, a device that can robustly and continuously monitor respiration is highly desirable. Monitoring of respiration may include determination of any one or more parameters indicating the extent to which a subject is breathing, such as respiratory rate (RR), minute volume (MV), tidal volume (TV) and/or other indications.

As one example of a suitable device, given the characteristics of opioid-induced respiratory depression (OIRD) mentioned above, a respiratory monitoring device would desirably be capable of monitoring respiration for up to 48 hours, be wearable and non-invasive so it gives full mobility and comfort to the patient during the length of its use, be easy to install and use, and be able to measure respiration at respiratory rates below 30 breaths per minute (BPM), such as within a range of 6 to 30 BPM.

Some conventional devices utilize surface electrodes that measure changes in intrathoracic impedance or that measure the electrical activity of respiratory muscles. While these devices offer a way to non-invasively measure RR, they are susceptible to artifacts from patient movement and they are unable to capture obstruction events in which the patient is trying to breathe but cannot (in contrast to respiratory depression, in which the patient's urge to breathe is reduced). Furthermore, these devices require time-consuming calibration by medical personnel to accurately measure RR.

Some conventional devices are based on pulse oximeters, which non-invasively measure blood oxygen saturation by measuring absorption or reflection of light from blood vessels. These devices are, however, unable to accurately measure RR below around 10 BPM, which includes a range of breath rates directly associated with respiratory depression. Further, oxygen saturation in the bloodstream may take several minutes to fall below critical levels after a respiratory incident. As such, pulse oximeters are poor devices for the early detection of respiratory depression events.

Some conventional devices deploy air collectors, typically in a face mask or mouthpiece, that measure the temperature, humidity and/or $CO_2$ composition of exhaled air. These devices are generally uncomfortable for the patient to wear and compromise the ability of the patient to move around freely. Thermal image processing devices, which measure the temperature variation around the nose of a patient using a thermal imaging camera have also been deployed, however these devices are susceptible to occlusion by intervening objects or when the patient changes position. Accordingly, the imaging devices also limit the ability of the patient to move around freely.

The inventors have recognized and appreciated techniques that mitigate the above-described problems with conventional devices. In particular, the inventors have developed a wearable device that includes multiple thermal sensors thermally coupled to one or more heat spreaders having a high thermal conductivity. The device may be small enough to be wearable between the mouth and nose of the patient, such as via an adhesive attachment to the upper lip. When the patient exhales, air is produced through the mouth and/or through the nose. Heat of the exhaled air may be accurately measured by the thermal sensors because each heat spreader absorbs heat of exhaled air as a result of its high thermal conductivity. Heat absorbed by each heat spreader can then thermally propagate, through the heat spreader, to thermal sensors coupled to that heat spreader. By measuring the change in temperature over time measured by the thermal sensors, the device allows respiration to be measured, which may include determining measures of respiration such as respiratory rate, minute volume and/or tidal volume of the patient.

According to some embodiments, the wearable device may comprise at least one controller configured to generate an indication of respiration of a patient by analyzing signals produced by one or more thermal sensors of the wearable device. In a preferred embodiment, the wearable device may comprise at least two thermal sensors so that heat produced from both the nose and the mouth may be measured by the device. Since a patient may breathe through some combination of the nose and the mouth, detecting heat from both sources may be highly desirable to accurately measure respiration. Irrespective of how many thermal sensors the wearable device includes, the at least one controller may include one or more processors (e.g., general purpose processors, microprocessors, etc.), Application-Specific Integrated Circuits (ASICs), Digital Signal Processors (DSPs) and/or Field Programmable Gate Arrays (FPGAs) arranged to receive indications of temperature from the thermal sensors and configured to generate an indication of respiration based on at least some of the received indications of temperature. For instance, a general purpose processor may be coupled to a computer readable medium comprising instructions, that when executed, cause the processor to generate said indication of respiration. Alternatively, an ASIC may be configured through circuitry to generate said indication of respiration. Irrespective of how the at least one controller is configured, the generated indication of respiration may include any information that is representative of respiration, and need not necessarily be a respiration rate. As non-limiting examples, the indication of respiration generated by the at least one controller may include a measure of oral temperature, a measure of nasal temperature, a differential measure of the nasal-oral temperature difference, a measure of an amount of exhalation (e.g., air flow rate) being produced, a measure of respiratory flow rate, or combinations thereof.

According to some embodiments, at least one controller of the wearable device may be further configured to determine a respiration rate of a patient by analyzing received indications of temperature from one or more sensors over time, and/or by analyzing indications of respiration generated by the at least one controller (examples of which are described above). For instance, an indication of an amount of exhalation may oscillate over time (e.g., sinusoidally or otherwise), and a respiration rate may be calculated by determining a period of the oscillations. In some embodiments, a respiration rate may be determined by analyzing received indications of temperature from one or more sensors by a device other than the wearable device, such as a computing device external to the wearable device. Such a computing device may receive data (e.g., indications of respiration) from the wearable device via a suitable wired and/or wireless connection and may determine a respiration rate of the patient based on the received data.

According to some embodiments, at least one controller of the wearable device may be further configured to determine a ventilation volume of a patient (e.g., tidal volume) and/or ventilation volume rate (e.g., minute volume) by analyzing received indications of temperature from one or more sensors over time, and/or by analyzing indications of respiration generated by the at least one controller (examples of which are described above). Such a calculation may, in some cases, be based on external factors such as a measurement of ambient temperature of the environment around the patient. In some embodiments, determining a ventilation volume and/or ventilation volume rate for a patient may be based upon a previously determined respiration rate for the patient. As used herein, a "ventilation volume" includes any measure of the amount of air inhaled and exhaled by a subject during a breath, and a "ventilation volume rate" includes any measure of the amount of air inhaled and exhaled by a subject over some period of time (e.g., volume per second, volume per minute, etc.).

In some embodiments, the wearable device may include an amplifier and/or a filter (e.g., a band pass filter). In producing an indication of respiration of a patient, the at least one controller of the wearable device may amplify one or more signals (e.g., signals received from one or more thermal sensors, and/or signals produced therefrom) and/or may apply filters to one of more the signals. Irrespective of which device calculates one or more measures of respiration (e.g., the wearable device and/or an external computing device), it may be desirable for the wearable device to amplify signals therein to produce a signal that is more easily analyzed by subsequent portions of the wearable device and/or other device. Similarly, it may be desirable for the wearable device to apply one or more filters to signals to reduce or eliminate transient signals and/or sources of noise. Amplifiers and/or filters may be implemented as software, hardware, or a combination of software and hardware, as the one or more controllers are not limited in this regard as discussed above.

According to some embodiments, the wearable device may include one or more displays configured to display a visual indication of a patient's respiration (e.g., respiratory rate, respiratory flow rate, ventilation volume, ventilation volume rate, etc.) determined by at least one controller of the wearable device. Such a display may include a digital display (e.g., LCD display); a plurality of lights, the number of which are an indication of respiration rate (e.g., 1 light=0-5 BPM; 2 lights=5-10 BPM; etc.) or respiratory flow (e.g., more illuminated lights for faster flow, fewer illuminated lights for slower flow; or a color that indicates respiratory flow rate); and/or a light that emits a color indicating a danger level of the current respiration rate (e.g., green for acceptable, yellow for at risk, or red for dangerously low).

In some embodiments, the wearable device may include one or more audio devices configured to produce an audible indication of a patient's respiration (e.g., respiratory rate, respiratory flow rate, ventilation volume, ventilation volume rate, etc.) determined by at least one controller of the wearable device. For instance, such an audio device may be configured (e.g., by receiving an appropriate signal from the at least one controller or otherwise) to produce an alarm tone if the respiratory rate determined by the at least one controller falls below some threshold (e.g., below 5 BPM), and/or may be configured to produce an audible indication of respiratory flow rate (e.g., higher pitched sound for higher rate and lower pitched sound for lower rate). Other measurements of respiration may be similarly presented through sound (e.g., an alarm tone may be produced when the ventilation volume or ventilation volume rate drops below a threshold, or the pitch of a sound may be selected based on a measurement of ventilation volume or ventilation volume rate).

According to some embodiments, the wearable device may include a strip of adhesive with which the wearable device may be attached to an upper lip of a patient. In some implementations, such a strip may be thermally insulating to reduce heat transfer to and/or from the wearable device from sources other than the exhaled air. In some embodiments, the wearable device may include mounts and/or attachments with which the wearable device may be attached to a patient. For instance, the wearable device may comprise hooks and/or clips to which a band or strap may be attached to fit the wearable device onto the patient's head. Such mounts and/or attachments may be provided in addition to, or alternatively to, the aforementioned adhesive. In some embodiments, the wearable device may include arms or other mounting points for attachment or mounting of other devices. For instance, the wearable device may include arms on its upper surface onto which an oxygen line may be fitted. As such, the wearable device may provide a convenient way for other devices to be attached to the patient in addition to the functionality described herein.

According to some embodiments, the wearable device may be configured to store determined indications of a patient's respiration and/or determined respiratory rates, ventilation volumes, etc. of a patient for a plurality of different times within at least one computer readable medium of the wearable device. For example, at least one controller of the wearable device may be configured to write indications of the patient's respiration, respiratory rates and/or ventilation volumes generated by the at least one controller to the at least one computer readable medium. Such data may be subsequently output from a suitable communication port of the wearable device for analysis. Such an approach may be particularly beneficial in utilizing the wearable device for analysis of a patient's respiration over time, such as in diagnosis and/or monitoring of sleep apnea of the patient.

Following below are more detailed descriptions of various concepts related to, and embodiments of, techniques for monitoring patient respiration. It should be appreciated that various aspects described herein may be implemented in any of numerous ways. Examples of specific implementations are provided herein for illustrative purposes only. In addition, the various aspects described in the embodiments below may be used alone or in any combination, and are not limited to the combinations explicitly described herein.

FIG. 1 depicts an illustrative wearable device, according to some embodiments. In the example of FIG. 1, wearable device 100 comprises a first thermal sensor 110 thermally coupled to a first heat spreader 111, and a second thermal sensor 120 thermally coupled to a second heat spreader 121. Both the first thermal sensor 110 and second thermal sensor 120 are electrically coupled to a controller 115, which is configured to generate an indication of respiration by analyzing signals produced by the thermal sensors, as described above. The wearable device may optionally include a communication device 126 to transmit the indication of respiration generated by the controller 115 to another device or devices, and/or may optionally include a display 127.

According to some embodiments, the first heat spreader and/or second heat spreader may be exposed on an exterior of the wearable device 100. To arrange the heat spreaders to absorb heat from the environment (e.g., from air surrounding the device 100), it may be beneficial to expose at least a portion of the heat spreaders to the environment. For example, either or both heat spreaders may protrude from the surface of the device or may be otherwise exposed through a hole in a housing of the device 100.

According to some embodiments, the first heat spreader and/or second heat spreader may comprise a material having a high thermal conductivity, such as but not limited to: copper, aluminum, silver, gold, nickel, silicon, ceramic, diamond, graphite, graphene, or combinations thereof. As discussed above, a heat spreader having a high thermal conductivity may be beneficial in that it increases the absorption of heat by the heat spreader from the environment and further improves transfer of heat from the heat spreader to one or more thermal sensors to which the heat spreader is coupled. In some embodiments, the heat spreader may have an uneven or rough surface exposed to the exterior of the device to increase the surface area of the heat spreader that can absorb heat from the surrounding environment.

According to some embodiments, the first thermal sensor and second thermal sensor may each be coupled to the first heat spreader and second heat spreader, respectively, in any manner that allows heat transfer from the heat spreader to the respective thermal sensor. For instance, the thermal sensor may be embedded within the heat spreader and/or may be adhered to the thermal sensor using a thermally conductive adhesive (e.g., a silicone resin glue, an epoxy resin glue, a polyimide resin glue, a ceramic glue).

According to some embodiments, thermal sensors 110 and 120 may include any component, or combination of components, configured to produce a signal indicative of its temperature. A thermal sensor may include, for example, a thermistor (e.g., an negative temperature coefficient (NTC) thermistor), a resistance thermometer (RTD), a thermocouple, a semiconductor-based sensor, or combinations thereof. While in the example of FIG. 1 a single thermal sensor is depicted as thermally coupled to each of the depicted heat spreaders, it will be appreciated that in general additional thermal sensors could be coupled to a given heat spreader and their signals transmitted to the controller 115.

According to some embodiments, controller 115 may be configured to generate an indication of respiration based on signals received from the first thermal sensor 110 and second thermal sensor 120. As discussed above, a controller so configured may include a processor (e.g., general purpose processors, microprocessors, etc.), Application-Specific Integrated Circuits (ASICs), Digital Signal Processors (DSPs) and/or a Field Programmable Gate Arrays (FPGAs) arranged to receive indications of temperature from the thermal sensors and configured to generate an indication of respiration based on at least some of the received indications of temperature. For instance, the controller 115 may be a general purpose processor coupled to a computer readable medium (not pictured in FIG. 1) comprising instructions, that when executed, cause the processor to generate said indication of respiration. Alternatively, the controller 115 may be an ASIC configured through circuitry to generate said indication of respiration. Irrespective of how the controller 115 is configured, the generated indication of respiration may include any information that is representative of respiration, and need not necessarily be a respiration rate. As non-limiting examples, the indication of respiration generated by the at least one controller may include a measure of oral temperature, a measure of nasal temperature, a differential measure of the nasal-oral temperature difference, a measure of an amount of exhalation being performed, and/or other indications.

According to some embodiments, controller 115 may be configured to determine a respiration rate based on received indications of temperature from the sensors 110 and 120, and/or by analyzing indications of respiration generated by the controller. For instance, an indication of an amount of exhalation may oscillate over time (e.g., sinusoidally or otherwise), and a respiration rate may be calculated by the controller 115 by determining a period of the oscillations.

According to some embodiments, controller 115 may be configured to determine a ventilation volume (e.g., tidal volume) and/or ventilation volume rate (e.g., minute volume) based on received indications of temperature from the sensors 110 and 120, and/or by analyzing indications of respiration generated by the controller. For instance, an indication of an amount of exhalation may oscillate over time (e.g., sinusoidally or otherwise), and a ventilation volume and/or ventilation volume rate may be calculated by the controller 115 based on how the received indications of temperatures vary over time (e.g., a mean value and/or an amplitude of temperature oscillations), a measurement of ambient temperature and/or a determined respiratory rate.

According to some embodiments, controller 115 may be configured to produce a digital signal (e.g., for transmission to another device via communication device 126) from an analog signal. For example, controller 115 may comprise analog electronics (e.g., an ASIC) configured to generate an indication of respiration based on signals received from the thermal sensors 110 and 120. Controller 115 may further comprise one or more components (e.g., a microcontroller, an analog-to-digital converter (ADC), etc.) configured to produce a digital signal from the generated analog indication of respiration.

According to some embodiments in which wearable device 100 includes communication device 126, the controller 115 may be configured to provide indications of temperature from the sensors 110 and 120, indications of respiration generated by the controller, and/or a determined respiratory rate (if the controller is so configured) to the communication device for transmission of said indications to an external device. The communication device may include any suitable wired and/or wireless communication technologies, such as but not limited to a Universal Serial Bus (USB) device, an Ethernet device, a wireless device (e.g., an IEEE 802.11 Wi-Fi device), a Bluetooth device, or combinations thereof.

According to some embodiments in which wearable device 100 includes display 127, the controller 115 may be configured to output signals to the display configured so that the display produces a visual indication of an indication of temperature received by the controller from the sensors 110 and/or 120, indications of respiration generated by the controller, and/or a determined respiratory rate (if the controller is so configured). Display 127 may include any suitable type or types of display, including one or more LEDs and/or a liquid crystal display. Signals output by the controller to the display 127 may be produced by the controller based on the type of display(s) provided within device 100. According to some embodiments, display 127 may be a liquid crystal display and controller 115 may be configured to display a visual indication of respiratory rate, ventilation volume and/or ventilation volume rate determined by the controller on the display via numeric digits or otherwise.

Figure 2:
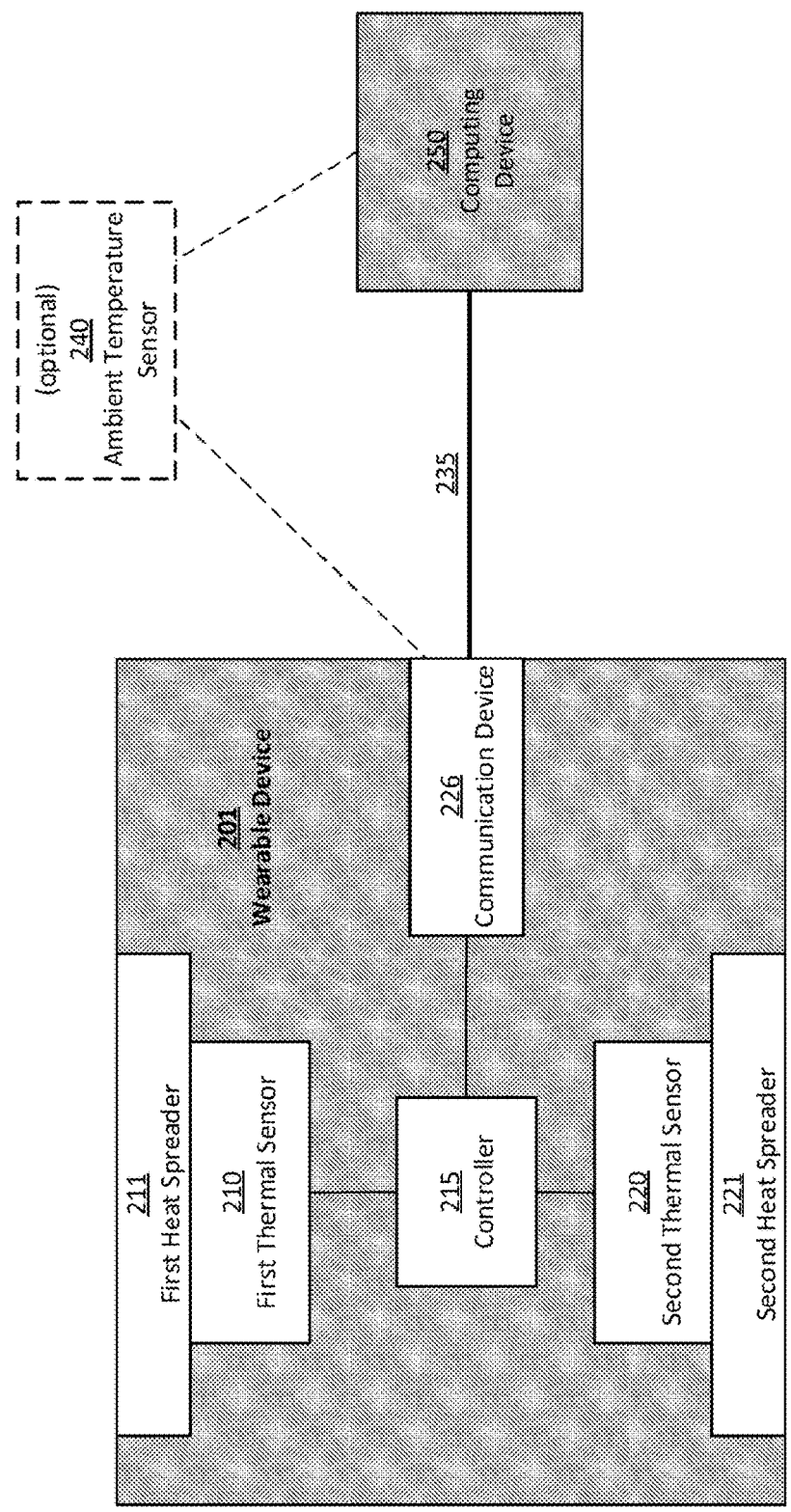
FIG. 2 depicts an illustrative system in which a wearable device communicates with a computing device, according to some embodiments.

FIG. 2 depicts an illustrative system in which a wearable device communicates with a computing device, according to some embodiments. System 200 is an illustrative example of a system in which device 100 communicates with an external device, in this case computing device 250 via a communication link 235. Elements 210, 211, 215, 220, 221 and 226 may, according to some embodiment, be configured via any of the above-described techniques with respect to elements 110, 111, 115, 120 and 121, respectively.

In some embodiments, computing device 250 may comprise software and/or hardware configured to monitor one or more patients by analyzing signals received from wearable devices worn by said patients. In some cases, an alarm may be generated by the computer device 250 when it is determined that respiration of a patient (e.g., a respiratory rate and/or ventilation volume) has dropped below a threshold level. As discussed above, values such as respiratory rate and/or ventilation volume may be calculated by the wearable device, by the computer device, or by both devices.

In some embodiments, system 200 may include an ambient temperature sensor 240. The sensor 240 may be configured to measure a temperature of the ambient environment close to the wearable device 201 in any suitable manner. In some embodiments, the temperature sensor 240 may be coupled to the wearable device 201 via a communication link and temperature readings from the sensor may be sent to the wearable device. In such cases, controller 215 may determine measures of respiration (e.g., ventilation volume) based on one or more received readings. In some embodiments, temperature sensor 240 may be coupled to the computing device 250 via a communication link and temperature readings from the sensor may be sent to the computing device. In such cases, computing device 250 may determine measures of respiration (e.g., ventilation volume) based on one or more received readings. In some embodiments, ambient temperature sensor 240 may be a component of the computing device 250.

To provide one illustrative way in which a wearable device as described above may be configured, FIGS. 3A-3D depict an illustrative design for a wearable device, according to some embodiments. The illustrative wearable device 300 includes a housing 301, which may be made of plastic (or similar) material with a low thermal conductivity. The device may be attached to the patient's skin via sticker 302, and/or through patches made of medical-grade adhesive tape that adhere to the face (e.g., the skin on the cheeks).

Top, front, bottom, and side projections of illustrative wearable device 300 are shown in FIG. 3B. Nasal heat spreader 303 and oral heat spreader 304 are installed inside the housing, where material is removed from the housing to allow for the exposure of the heat spreaders to the environment so that gas coming out of the nose and the mouth may be incident upon the heat spreaders (or at least so that heat from such exhalation may be otherwise absorbed by the heat spreaders via convection and conduction). The heat spreaders 303 and 304 may be thermally separated from one another so that heat incident upon one of the heat spreaders is blocked or inhibited from reaching the other heat spreader. For example, the nasal heat spreader 303 may be arranged so that, when the device is worn, little or no heat from the mouth reaches the nasal heat spreader. Similarly, the oral heat spreader 304 may be arranged so that, when the device is worn, little or no heat from the nose reaches the oral heat spreader.

The illustrative wearable device 300 may include heat spreaders formed from copper, as it has a high thermal conductivity as well as antimicrobial properties, which makes it ideal for medical purposes. Heat spreaders may take various shapes, and may have a design optimized by computer simulations to maximize the thermal transfer of heat from respiratory flow to the heat spreaders. In the case of the depicted illustrative wearable device 300, the shape of the heat spreaders is a thin rectangular plate. As shown, the heat spreaders are fixed from inside the housing, leaving a small clearance with the outer surface of the housing, to avoid direct contact with the skin.

In the illustrative wearable device 300, the heat spreaders 303 and 304 absorb and transfer heat coming from the respiration gas flow to thermal sensors 305 and 306, respectively. A cross-sectional view of the respiratory sensor is included in FIG. 3C, where a nasal thermal sensor 305 and an oral thermal sensor 306 are shown. Thermal sensors may be fixed to the surface of a respective heat spreader that is facing inside the housing. In the illustrative wearable device 300, thermal sensors 305 and 306 are thermistors, whose body is glued to the copper heat spreaders by means of a conductive ceramic glue.

Figure 3C:
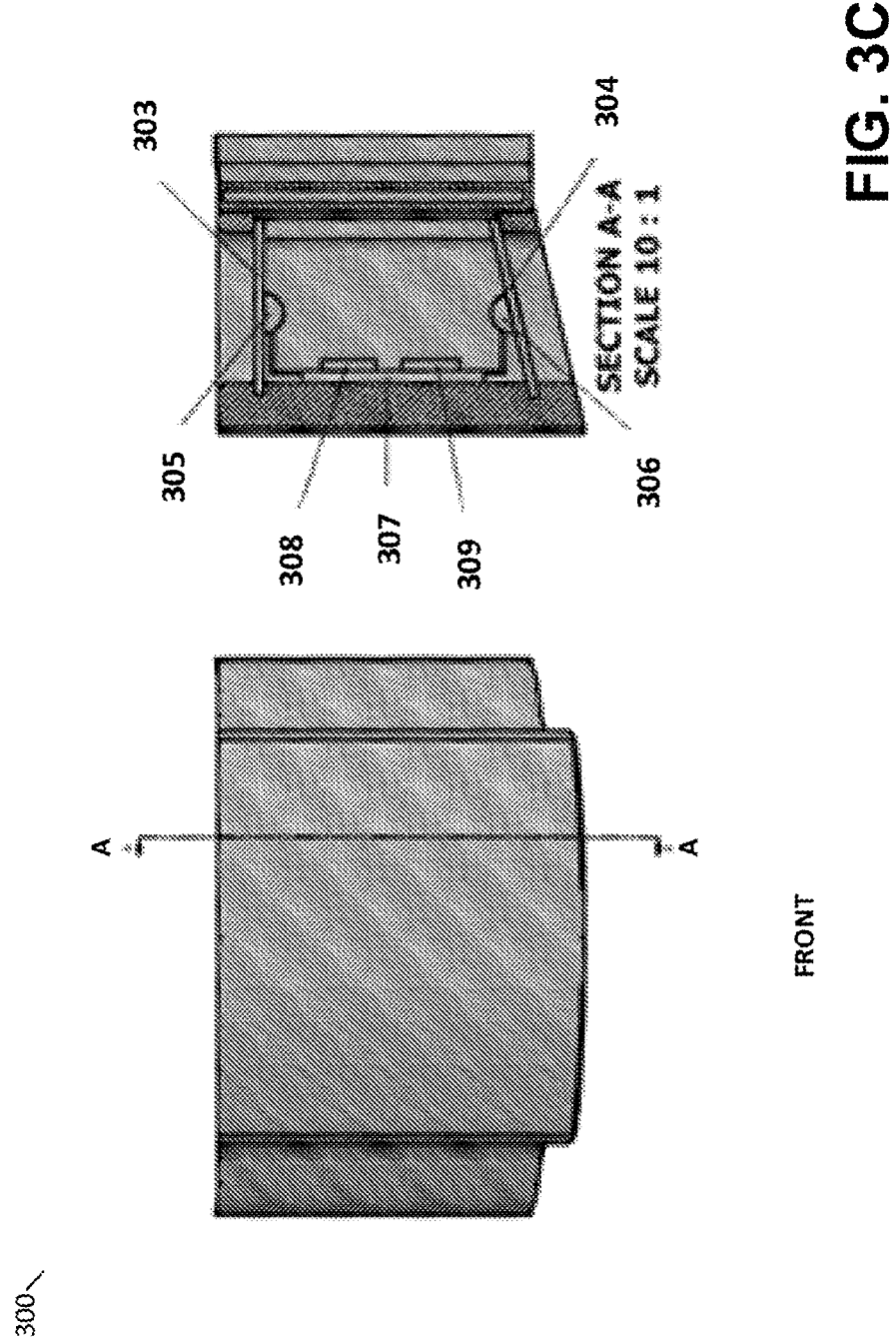
Figure 3D:
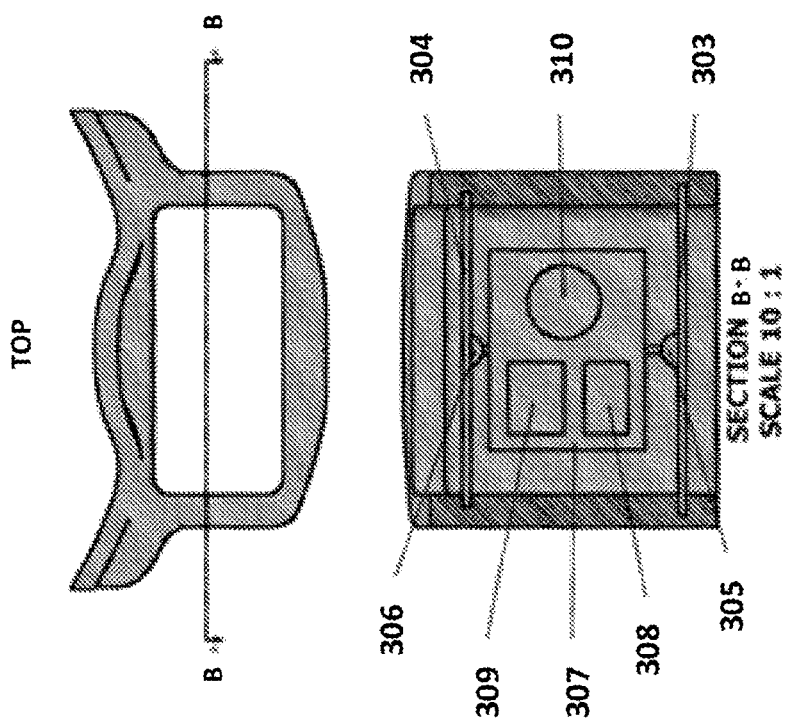
Figure 3E:
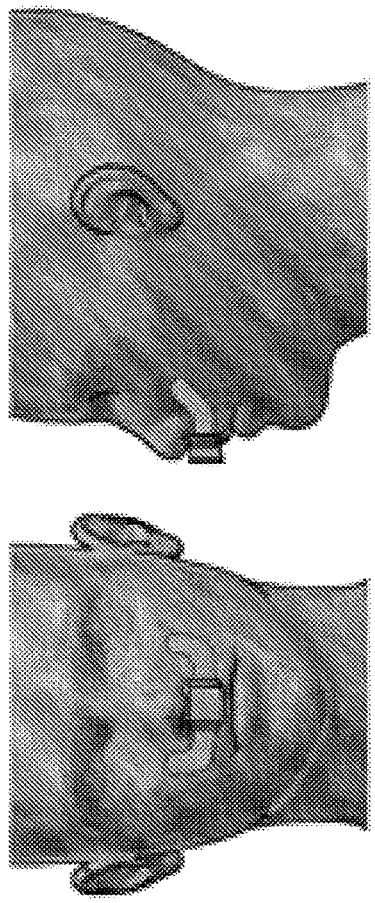

In the illustrative wearable device 300, temperature changes within respiratory flowing gas as the patient inhales and exhales will result in changes in the thermal sensor resistance, which may be transformed into electrical signals that are sent to a controller components 308 and 309 that are connected through a printed circuit board 307. The controller in the illustrative wearable device 300 includes component 308, which comprises: a Wheatstone bridge configuration coupled to the thermal sensors 305 and 306, wherein the circuit outputs a differential voltage related to the temperature changes in the heat spreaders; and a bandpass filter for signal conditioning. Controller component 309 comprises an analog-to-digital converter (ADC) integrated in a microcontroller configured to convert the analog voltage signal into digital data, which may be processed to obtain respiratory flow parameters. In some embodiments, the microcontroller may include a wireless (e.g., Bluetooth) link to communicate with an external monitor. Alternatively, or additionally, the device may include a connector through which a wired link (e.g., USB cable) to an external monitor is established. The cable carries the measured signals from the sensor to the external monitor, and also powers the electronics in the device from a voltage source located at the external monitor. The electronics are powered by means of a battery 310, which can be seen in FIG. 3D. FIG. 3E depicts how the illustrative device of FIGS. 3A-3D may be installed on the upper lip of a patient.

Figure 16:
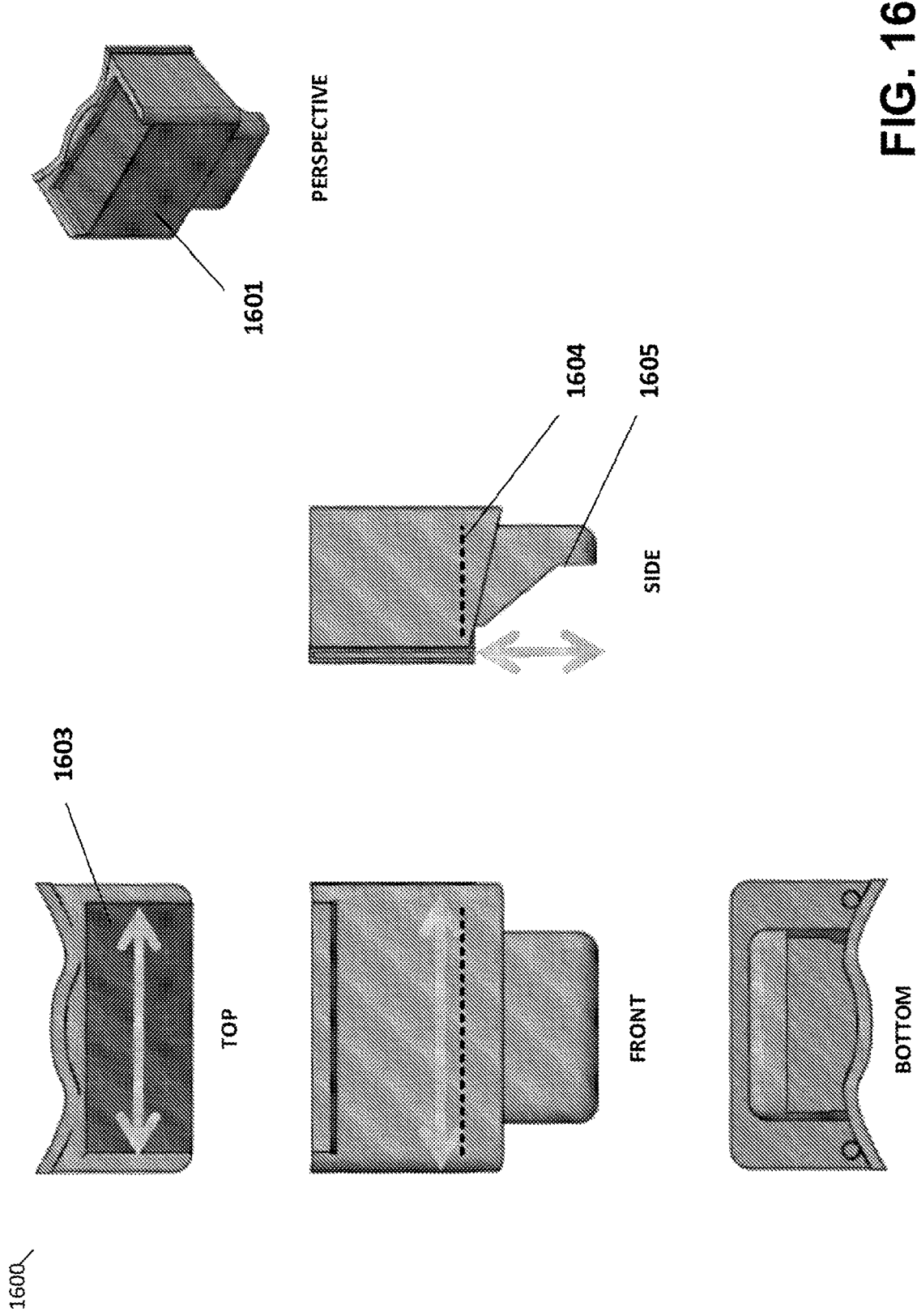
FIG. 16 depicts an alternative illustrative design for a wearable device, according to some embodiments.

FIG. 16 depicts an alternative illustrative design for a wearable device, according to some embodiments. As with the example of FIGS. 3A-3D, the illustrative wearable device 1600 includes a housing 1601, which may be made of plastic (or similar) material with a low thermal conductivity. The device 1600 may be attached to the patient's skin via a sticker, and/or through patches made of medical-grade adhesive tape that adhere to the face (e.g., the skin on the cheeks).

Top, front, bottom, side and perspective projections of illustrative wearable device 1600 are shown in FIG. 16. Nasal heat spreader 1603 and oral heat spreader 1604 are installed inside the housing, where material is removed from the housing to allow for the exposure of the heat spreaders to the environment so that gas coming out of the nose and the mouth may be incident upon the heat spreaders (or at least so that heat from such exhalation may be otherwise absorbed by the heat spreaders via convection and conduction). In the example of FIG. 16, the oral heat spreader 1604 is installed deeper within the housing compared with the device 300 of FIGS. 3A-3D and the housing includes an opening within an oral receptor region 1605. The opening acts to collect exhaled air and funnel it onto the oral heat spreader 1604 which, in FIG. 16, is shown as a dashed line since in the illustrated projections the oral heat spreader is not visible from the exterior of the device.

The above discussion of the heat spreaders of FIGS. 3A-3D in addition to operation of the device 300 may also be applied to the heat spreaders of FIG. 16 and to the device 1600, respectively.

Figure 4:
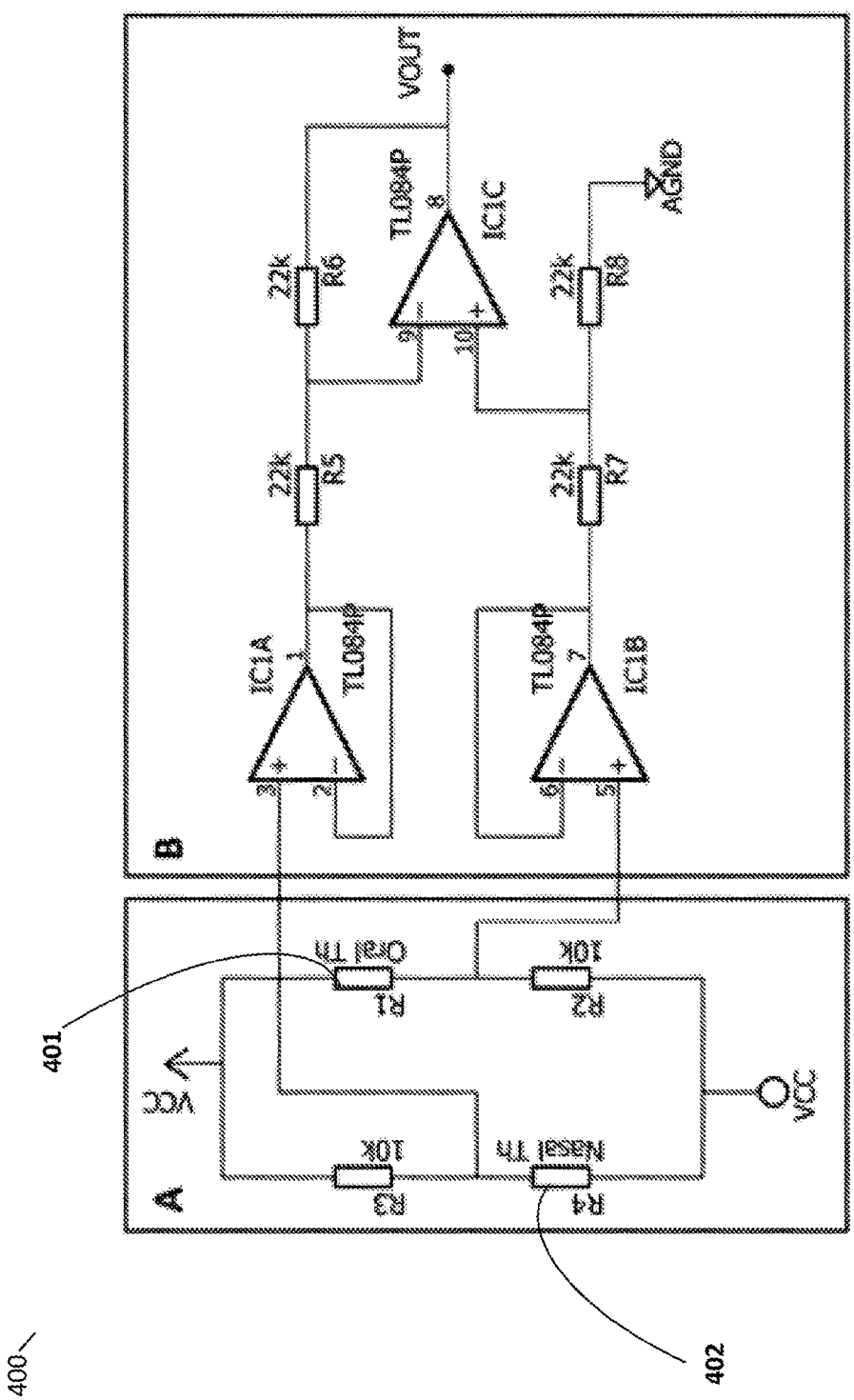
FIG. 4 is an illustrative circuit suitable for producing an indication of respiration based on signals produced from two thermal sensors, according to some embodiments.

FIG. 4 is an illustrative circuit suitable for producing an indication of respiration based on signals produced from two thermal sensors, according to some embodiments. Any of the illustrative devices 100, 201 and/or 300 may include circuit 400 (e.g., as some or all of controllers 115, 215, 308 or 309, respectively), which is configured to produce a differential voltage based on a temperature difference measured by thermal sensors 401 and 402, representing oral and nasal temperatures, respectively. As such, in this illustrative circuit, an indication of respiration generated by the circuit is a differential signal that represents a temperature difference between two thermal sensors. As shown, the thermal sensors are configured in a Wheatstone bridge topology in section A, whose outputs are provided to a differential amplifier in section B.

Figure 5:
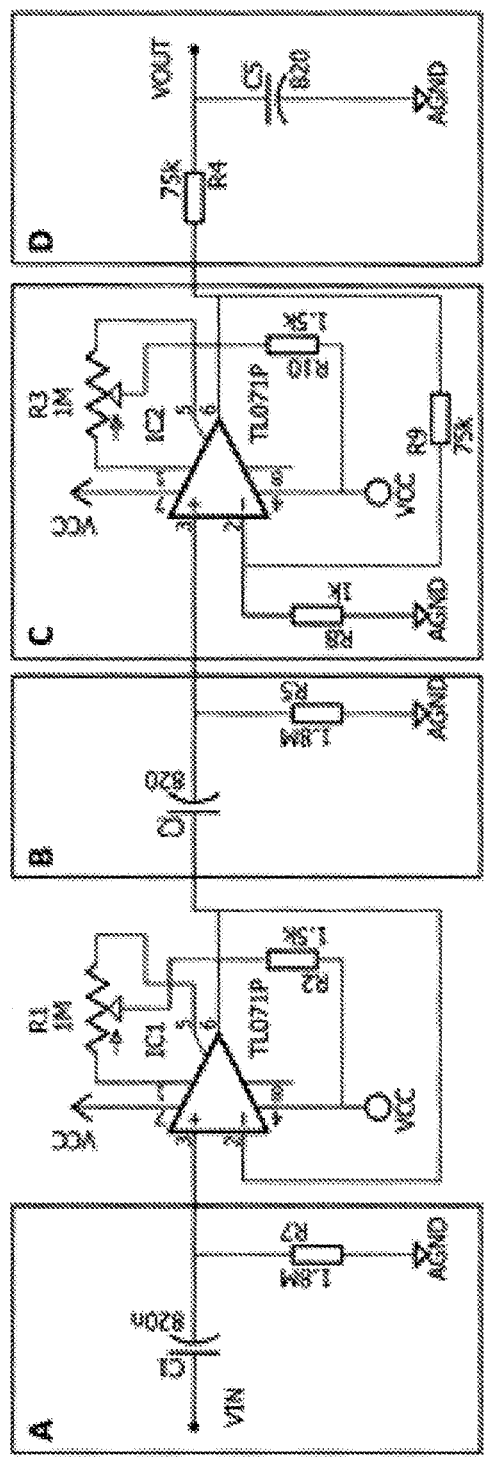
FIG. 5 is an illustrative filter and amplifier circuit for processing signals produced from thermal sensors, according to some embodiments.

FIG. 5 is an illustrative filter and amplifier circuit for processing signals produced from thermal sensors, according to some embodiments. As discussed above, there may be a benefit to filtering and/or amplifying an indication of respiration generated by (or within) a controller. The illustrative circuit 500 may be included in any suitable controller to filter and amplify any suitable indication of respiration generated based on signals produced by thermal sensors. For example, the input to circuit 500 may be, but is not limited to, the output differential voltage signal produced by circuit 400. In the example of FIG. 5, the filter is a 3-pole bandpass filter with cutoff frequencies of 0.1 Hz and 2.5 Hz. The voltage amplifier stage has a gain of 76.

Figure 6:
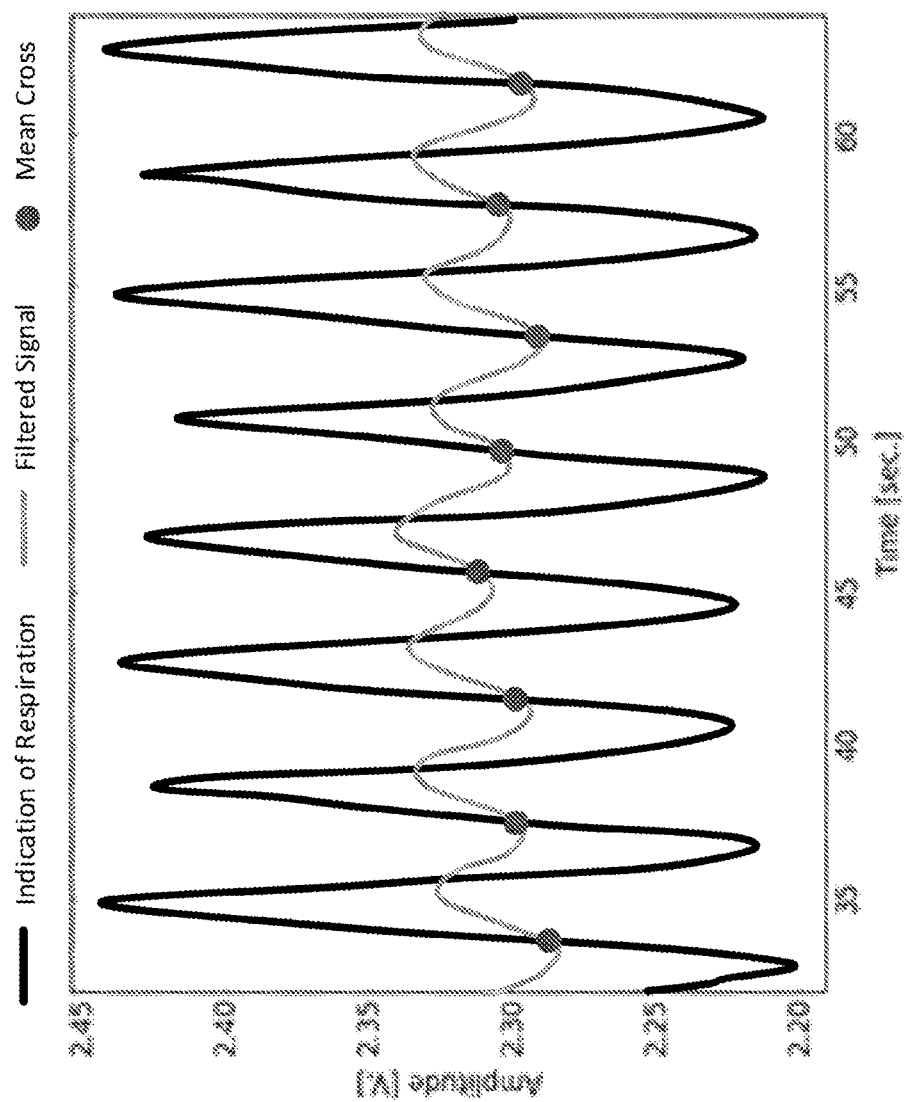
FIG. 6 illustrates data used for estimation of respiratory rate based on an oscillating indication of respiration, according to some embodiments.

FIG. 6 illustrates data used for one exemplary estimation of respiratory rate based on an oscillating indication of respiration, according to some embodiments. FIG. 6 and the description below provide one illustrative way in which respiratory rate may be measured from an indication of respiration produced by a controller of a wearable device. The described estimation process may be performed by a controller of a wearable device and/or by an external device (e.g., a computing device receiving the indication of respiration from the wearable device) such as, but not limited to, controllers 115, 215, 308 or 309 described above.

In the example of FIG. 6, the mean-crossing algorithm is used to estimate the respiratory rate (RR). In the illustrative example of FIG. 6, a moving window of 5 seconds is used to apply a digital averaging filter to the indication of respiration produced by the wearable device (black) to obtain a filtered signal (grey). Then, the positive intersections between the indication of respiration signal (ascending) and the filtered signal are marked as a beginning of a respiratory cycle. Respiratory cycle periods may then be calculated from the obtained marks.

In some embodiments, a time window of 30 seconds may be utilized to compute the mean respiratory cycles periods in order to estimate the mean respiratory rate. The algorithms may update the mean RR periodically, such as every 1 second. However, other suitable values of the time window, moving window and/or update period may also be utilized.

As one illustrative technique by which indications of ventilation volume and/or ventilation volume rate—in particular, the tidal volume (TV) and/or respiratory minute volume (MV)—may be estimated, the following description is provided. The tidal volume is the volume of air displaced between normal inhalation and exhalation, whereas the respiratory minute volume is a volume rate of air so displaced in the time span of one minute. A relationship between RR, MV and TV is MV=TV×RR.

To estimate MV and TV from temperature signals acquired by sensors of a wearable device, a relation may be established between temperature parameters such as the temperature average value (DC), temperature oscillation amplitude (AC), ambient temperature ($T_{amb}$), and respiratory rate (RR). As one example, this relationship may be established via computational fluid dynamics and heat transfer simulations which solve the Navier-Stokes equations and the heat equation. Suitable assumptions may be included in such a simulation, such as assuming an incompressible and viscous fluid flow for the air, and a conductive material for the heat spreader in the sensor.

It has been observed that an accurate calculation of MV may be calculated according to the following relationship:

$$\log_{10} MV = 1.8994 \log_{10} AC + 2.8920 \log_{10} RR - 0.2907 DC + 0.1916 T_{amb} - 28.3850$$

where MV is a calculated minute volume in l/min (liters per minute), AC is an observed amplitude of temperature oscillations measured by one or more temperature sensors of the wearable device in degrees Celsius, RR is a respiratory rate of the wearer of the device in breaths per minute (BPM) (which may be calculated from measurements produced by the same device as described herein, or otherwise), DC is an observed mean temperature measured over some period of time by one or more temperature sensors of the wearable device in degrees Celsius, and $T_{amb}$ is a measured ambient temperature (e.g., measured via temperature sensor 240 shown in FIG. 2). Tidal volume in units of liters may be calculated via an equivalent formula as for MV using the relationship MV=TV×RR.

Another approach to estimate the tidal volume (TV) from temperature measurements made by the thermal sensors may be based on conjugate heat transfer theory. Within this illustrative framework, the heat transfer taking place in a conductive plate subject to forced convective flow can be modeled by the equation:

$$c_p \rho_c \dot{T} h + (T_s - T_r) Nu(u) k_a / D = 0,$$

where u is the airflow velocity magnitude, $c_p$, $\rho_c$ and h are the copper plate heat capacity, density and thickness, respectively, $\dot{T}$ and $T_s$ are the time rate of change of temperature and the temperature of the copper plate surface, whereas $T_0$ is the temperature of the respiration impinging jet. Values $k_a$ and D are the air thermal conductivity and characteristic length of the air flow. Finally, Nu(u) the Nusselt number of the heat transfer setup, which indicates the ratio of convective to conductive heat transfer, depending on the characteristics of the flow and geometry.

Following Strieg and Diller, (1984), the local Nusselt number for an impinging jet on a flat surface can be calculated as:

$$Nu_x = 1.64 Re^{1/2} a_L \left(\frac{d}{L}\right)^{3/4} \left(1 - 2.89\left(\frac{x}{L}\right)^2\right)(1 - F) + a_c \left(1 - 3.86\left(\frac{x}{L}\right)^2\right)\left(\frac{d}{L}\right)^{1/2} F$$

where Re=uD/μ is the Reynold's number, which characterizes the flow in terms of the flow velocity u, a characteristic diameter d (in this case, the nostril width) and the air kinematic viscosity μ. x is the distance away from the axis of the impinging yet, whereas L is the sensor distance to the nostril. Variables $a_L$ and $a_c$ are parameters fitted to model the operating temperature. Finally, F is the entrainment factor, which normalizes the surface temperature $T_s$ in terms of the room temperature $T_\infty$ and the jet temperature $T_0$:

$$F = \frac{T_0 - T_\infty}{T_0 - T_s}$$

The Nusselt is corrected to its transient average $\underline{Nu}$ on a sinusoidal cycle as $$\underline{Nu} \simeq Nu_x \left(1 - 0.0724 \frac{u_c^2}{u_\infty^2}\right)$$

where $u_c$ and $u_\infty$ represent the sinusoidal wave amplitude and the averaged velocity, respectively. These equations define a non-linear empirical relation between the sensor temperature and the fluid flow, from which the TV can be calculated by numerically integrating within the exhalation time window.

Illustrative Experiment: Setup

While numerous embodiments of the present invention have been described above, an illustrative pilot study is described below to further illustrate advantages of embodiments of the present invention. The below description should not be seen as limiting with respect to any particular embodiment, and is provided merely as an example.

Figure 7:
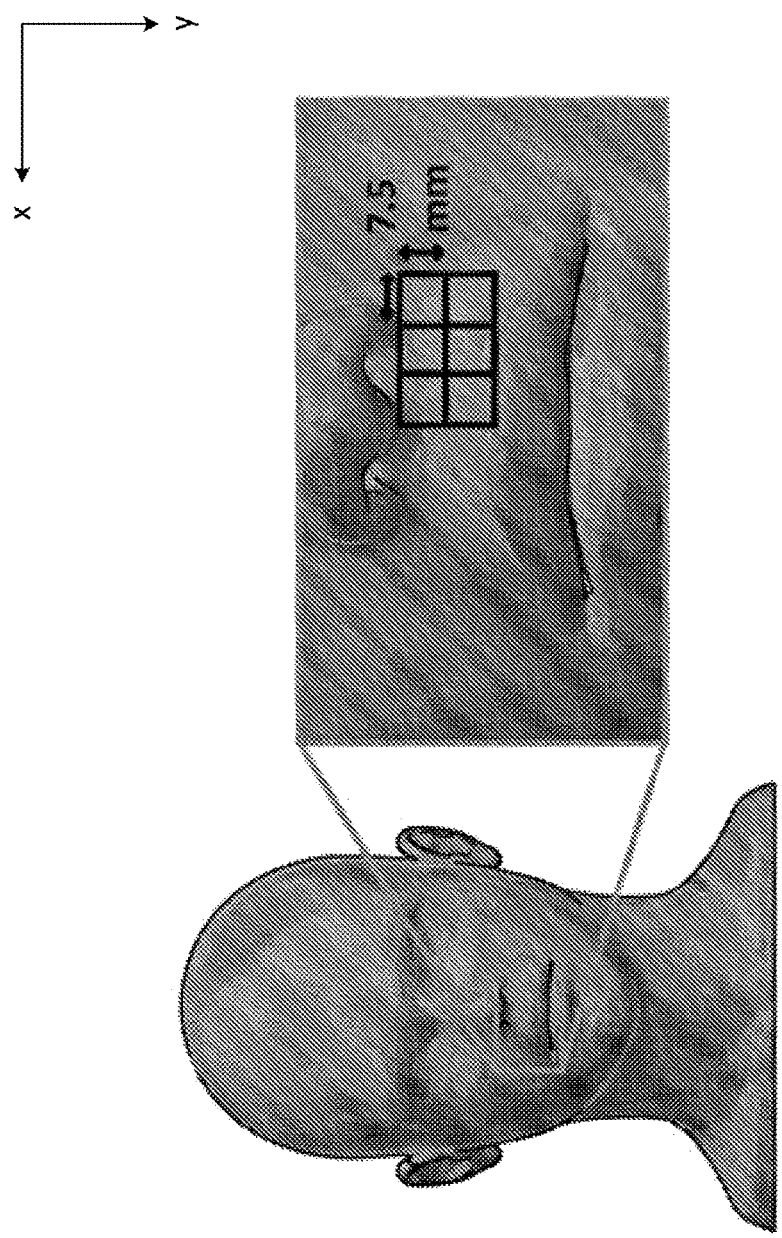
FIG. 7 depicts position markers for a sensitivity test performed within illustrative pilot study, according to some embodiments.

Position sensitivity test: To test the sensitivity of the wearable device to position on a patient, we acquired respiratory signals at several positions in a reticle marked on the face of a subject volunteer, as shown in FIG. 7, using both the wearable device as shown in FIGS. 3A-3D and a single-thermistor sensor. In this example, the reticle size is 7.5 mm by 7.5 mm square and was placed in a variety of different positions as shown during the test. Initially for the purposes of this test, the subject was breathing following a precise metronome set at 6 and 15 bpm for a period of 1 minute. Respiratory flow signals acquired by the wearable device were then processed to compute respiratory rate (RR), signal-noise ratio (SNR) and maximum signal amplitude. This protocol was repeated using the single-thermistor sensor (e.g., NTC 10 k thermistor, Vishay Components), for which the same outputs were recorded, in order to compare both performances.

Human pilot study: To assess the performance of an illustrative wearable device, 17 healthy subject volunteers were recruited for a pilot study. Anthropometric data was collected. Inclusion criteria included i) subjects with age between 18-65 yrs old, ii) non-smokers, iii) no record of chronic pulmonary disease, and iv) no allergies to copper. The breathing sensor was installed on all subjects (e.g., as depicted in FIG. 3E), and indications of respiratory rate produced from the wearable device was continuously measured during the whole duration of the study. Additionally, a pulse oximeter (Particle sensor, MAX30105, Sparkfun) and chest band (Stretch sensor, RB-Ada-34, Adafruit Industries) were installed on the subjects to continuously record the peripheral oxygen saturation (SpO2), heart rate (HR), and thorax movement. During the experiment, visual counting of respiratory cycles was recorded by means of a person pressing a button. All subjects were requested to lay down on a stretcher in supine position.

The following tests (in chronological order) were performed for each subject during the study:
1. Guided breathing test: Subjects were asked to breathe using his/her nose for one minute following a metronome at 6, 8 and 10 bpm. The experiment was then repeated for oral breathing, with nasal flow blocked by using nose pins.
2. Spontaneous breathing test: Subjects were asked to rest and breathe spontaneously during 10 minutes.
3. Erratic breathing test: after a period of 1 minute of spontaneous breathing, subjects were asked to hold their breath as long as it was comfortable for them. After a second period of one minute of normal breathing, subjects were asked to breathe against a closed glottis for as long as they could to simulate obstructed breathing.

Data analysis for the recorded respiratory signals was performed according to the example of FIGS. 4-6. The relative error for the moving time window 'i' was calculated as $$\text{Error}_i [\%] = \frac{RR_{i,meas} - RR_{i,ref}}{0.5 * (RR_{i,ref} + RR_{i,meas})}$$

where $RR_{i,ref}$ is the reference value of RR obtained from visual counting, and $RR_{i,meas}$ is the RR obtained from the wearable device's measurements. The bias is defined as the average of the set of relative errors (i=1, ..., $N_{windows}$), the precision is the standard deviation of the set of relative errors, and the accuracy is defined as the root mean square value of the relative error set.

Illustrative Experiment: Results

Position Sensitivity Tests

Figure 8A:
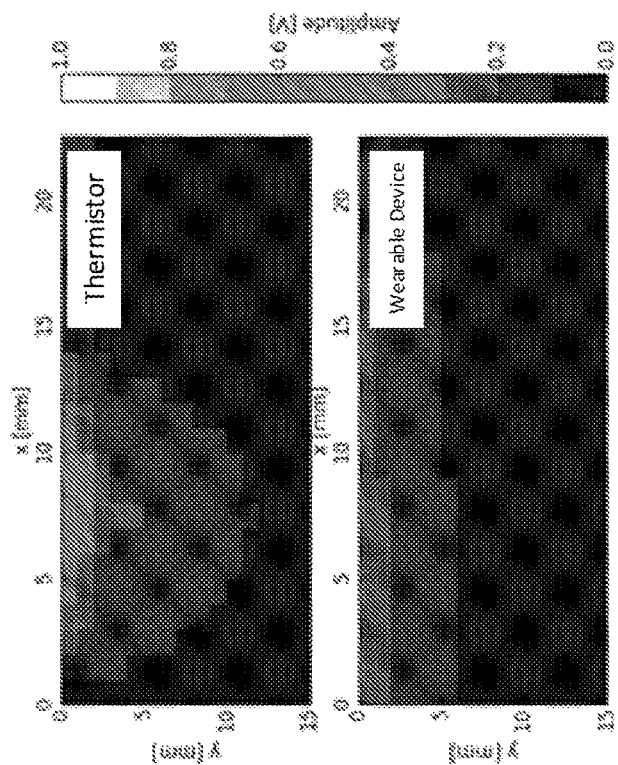
FIGS. 8A-8B are heat map diagrams of signal amplitude measured in the illustrative pilot study based on positions of a thermistor and position of the wearable device during guided breathing, according to some embodiments.
Figure 8B:
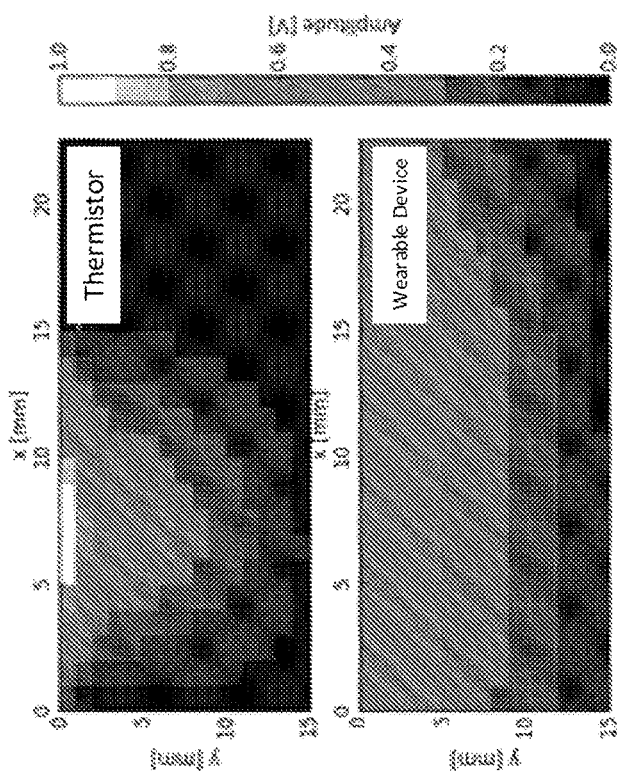

The maximum amplitude of the respiratory signal for different positions measured in the single-thermistor sensor and the wearable device are shown in FIG. 8A for a respiratory frequency of 6 BPM and FIG. 8B for a respiratory frequency of 15 BPM. Values measured at markers were interpolated to improve the figure interpretation. For the single-thermistor sensor at both respiratory rates, the signal amplitudes are high in the region right below the nostril, but quickly decrease as the thermistor is located away. In contrast, the wearable device delivers, in general, a lower signal amplitude that decrease at slower rates as the sensor is located farther away from the nostrils.

Figure 9A:
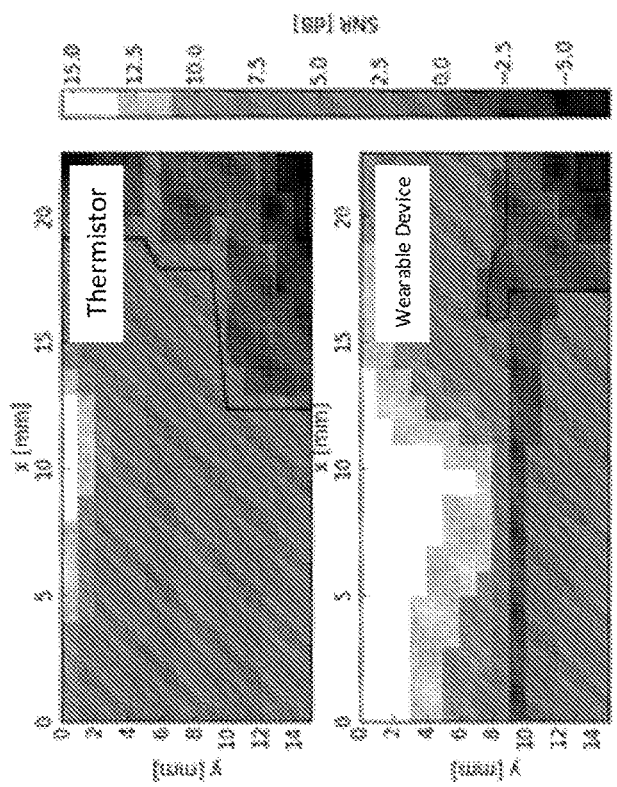
FIGS. 9A-9B are heat map diagrams of signal-to-noise ratio measured in the illustrative pilot study based on positions of a thermistor and position of the wearable device during guided breathing, according to some embodiments.
Figure 9B:
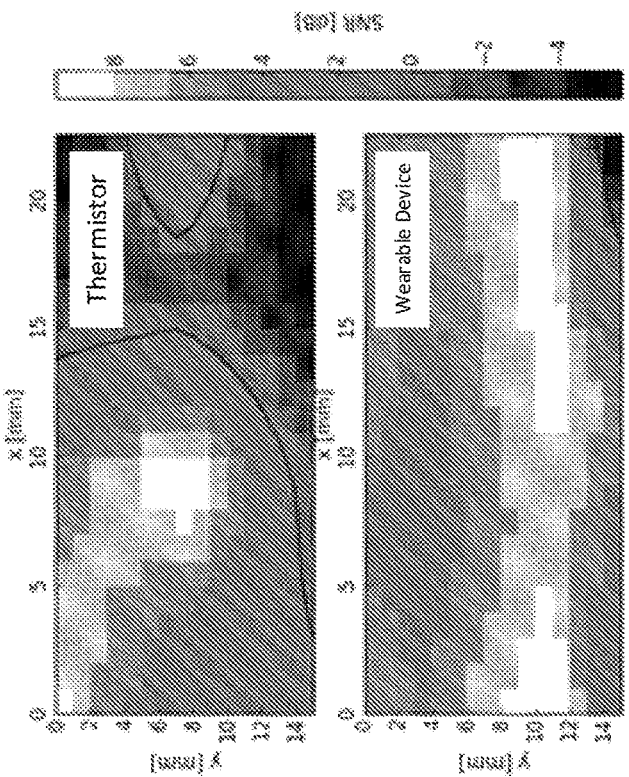

The signal-to-noise ratio was computed for all locations considered in the sensitivity study, which are reported in the map of FIG. 9A for the case of a respiratory rate of 6 BPM and FIG. 9B for 15 BPM. A solid line is plotted in all figures for the level set where SNR=0, indicating regions where the signal and the noise have the same amplitude. In both cases, the wearable device SNR distribution is positive for roughly all the region under study, with the exception of a small region far down and right. In contrast, the thermistor has positive SNR values close to the nostrils, and quickly decays as it is located farther away.

Figure 10A:
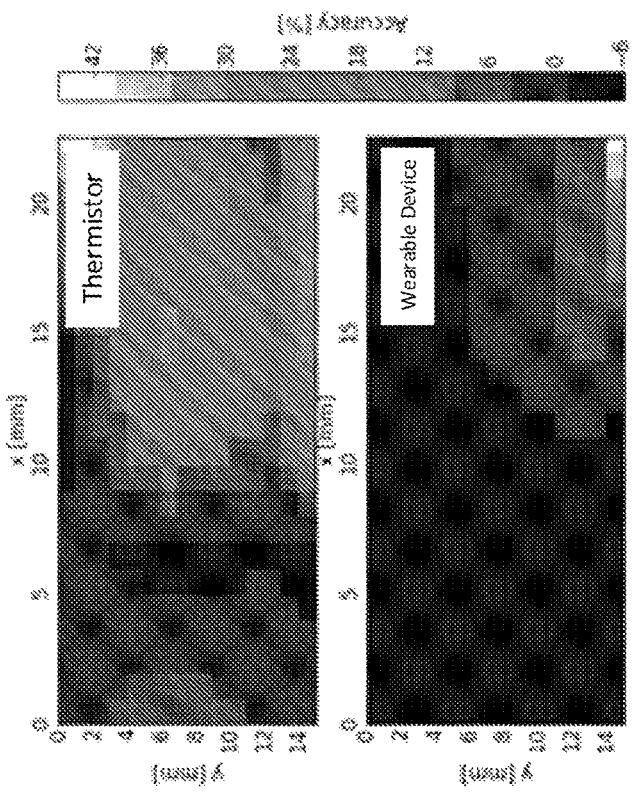
FIGS. 10A-10B are heat map diagrams of accuracy measured in the illustrative pilot study based on positions of a thermistor and position of the wearable device during guided breathing, according to some embodiments.
Figure 10B:
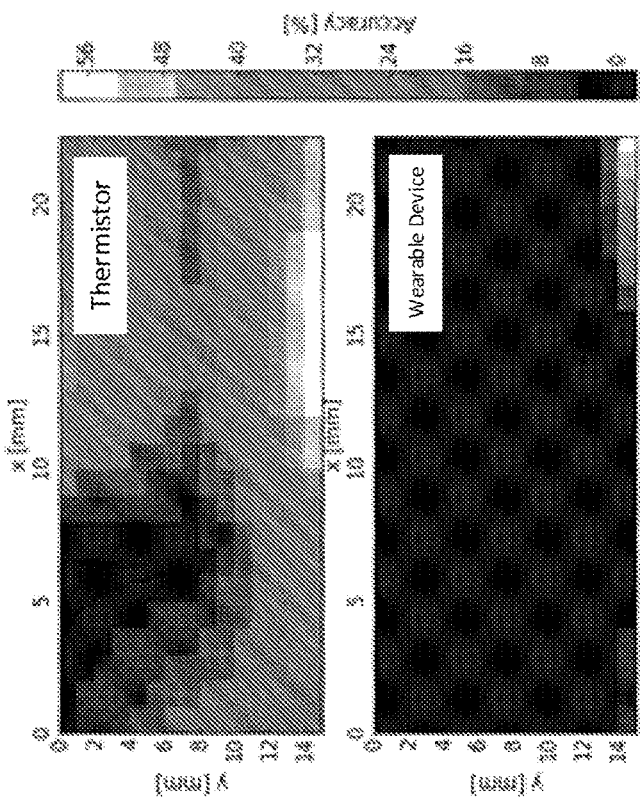

The maps with accuracy values for guided breathing at 6 BPM and 15 BPM are reported in FIG. 10A and FIG. 10B, respectively. For the wearable device, the accuracy is always less than roughly 5% in the entire region of study, with the exception of a very small area in the bottom right corner. In contrast, the single-thermistor sensor only achieves accuracy values less than 5% in a reduced region directly under the nostril, out of which accuracy rapidly increases up to values of 40%.

Human Pilot Study

Figures 11A, 11B:
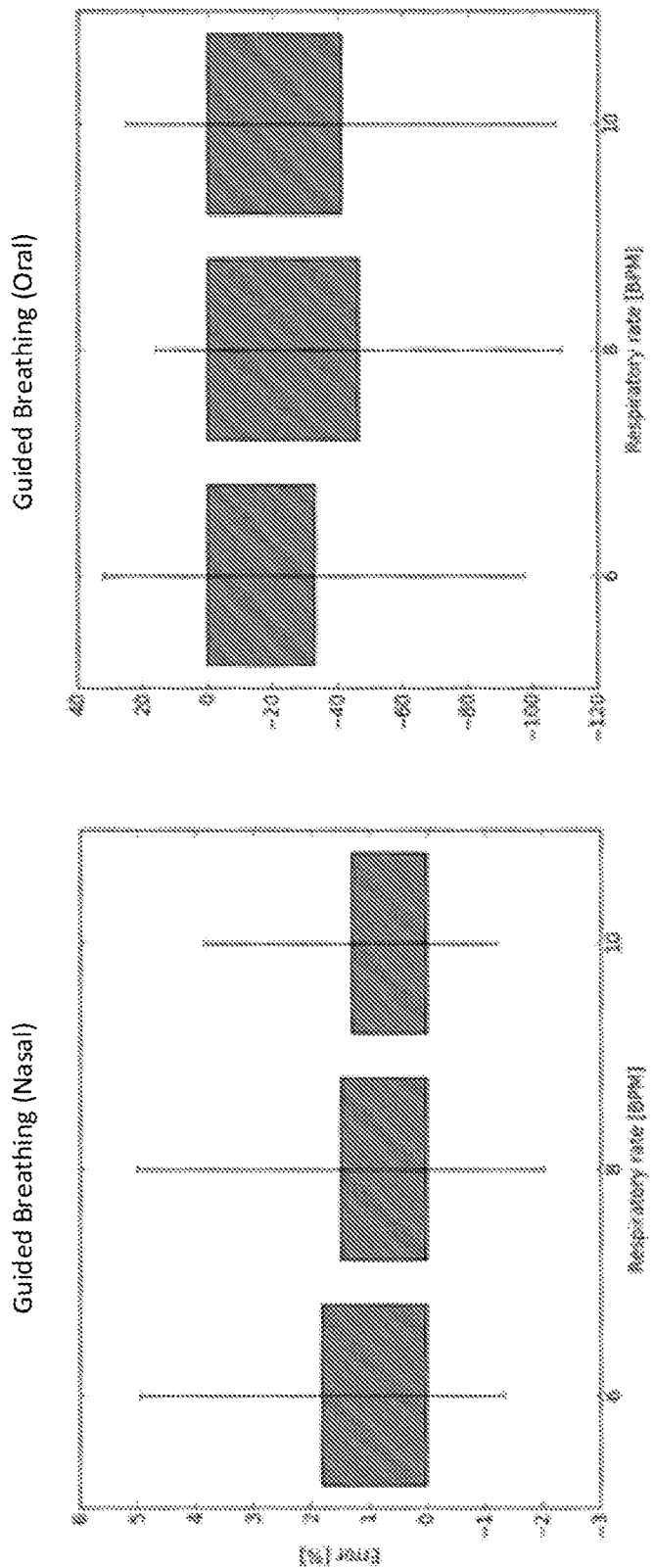
FIGS. 11A-11B illustrates accuracy of determining respiratory rates using a wearable device during guided breathing, according to some embodiments.

The bias and precision values for the sample group under guided breathing at 6, 8 and 10 BPM is reported in FIG. 11A for nasal breathing and FIG. 11B for oral breathing. In the case of nasal breathing, the bias for the sample group is less than 2% and the precision less than 4% for all respiratory rates. The case of oral breathing displays a much higher bias with values as high as 43% (absolute value), as well as larger precision reaching 66%.

Figure 12B:
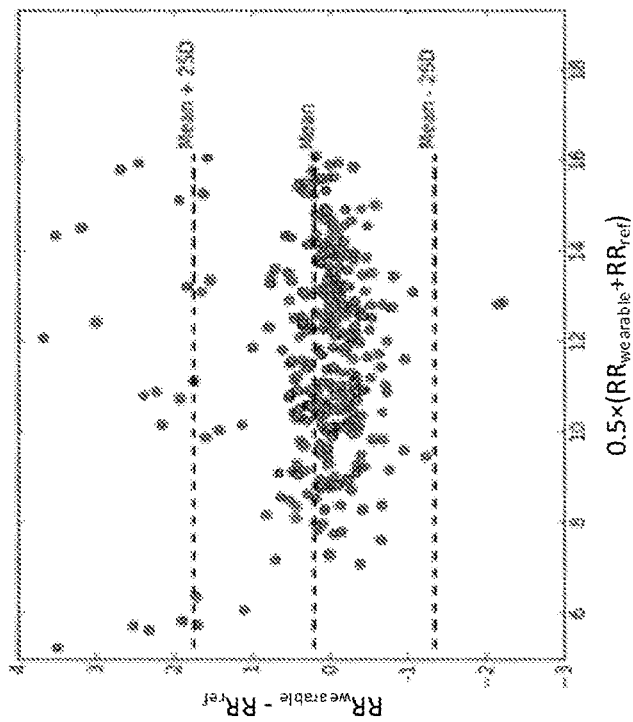
FIG. 12B depicts a Bland-Altman plot for assessing the agreement of respiratory rate determined using the wearable device and a reference method for a single test subject, according to some embodiments.
Figure 12A:
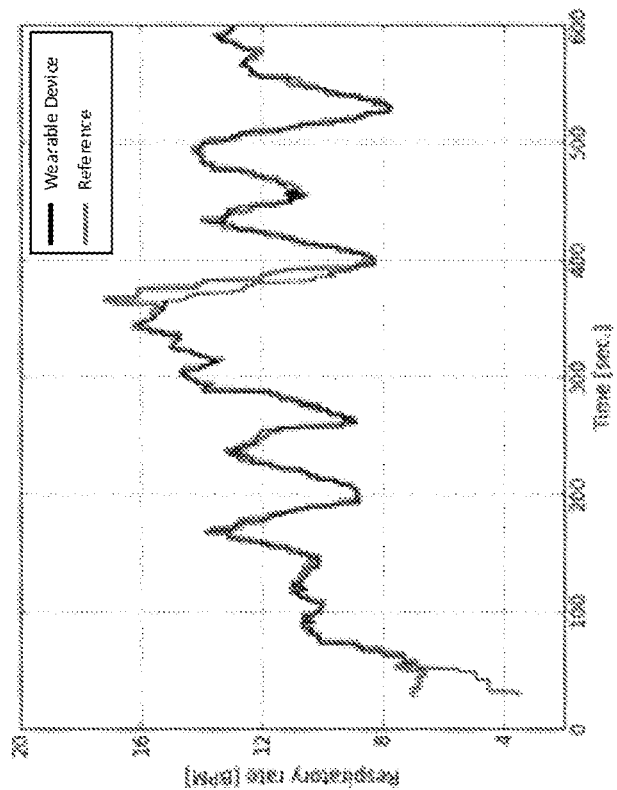
FIG. 12A depicts measured respiratory rates over time compared with a reference value for a single test subject, according to some embodiments.
Figure 13:
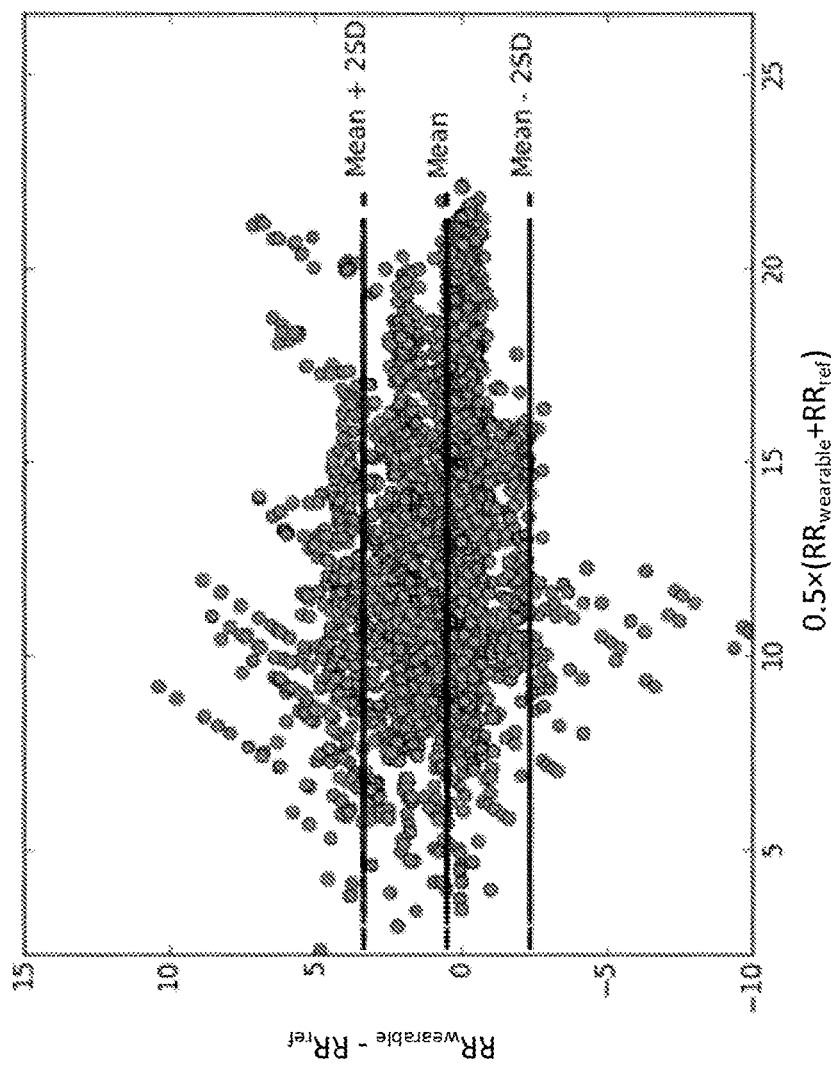
FIG. 13 depicts a Bland-Altman plot for assessing agreement of respiratory rate determined using the wearable device and a reference method for a subject group, according to some embodiments.

The time evolution of the respiratory rate determined based on the indication of respiration produced by the wearable device and determined via the reference method (visual counts) for subject 8 of the sample group spontaneously breathing in rest conditions is reported in FIG. 12A. The RR calculated based on measurements taken by the wearable device closely follows the reference values during the entire time frame, with slight deviations at the beginning of the experiment. To assess the agreement between the wearable device and the reference method, a Bland-Altman plot is included in FIG. 12B, where the mean difference is 0.19 BPM. The Bland-Altman plot that considers the entire sample group presented in FIG. 13 where the average difference between the wearable and the reference method is 0.47 BPM.

Figures 14A, 14B:
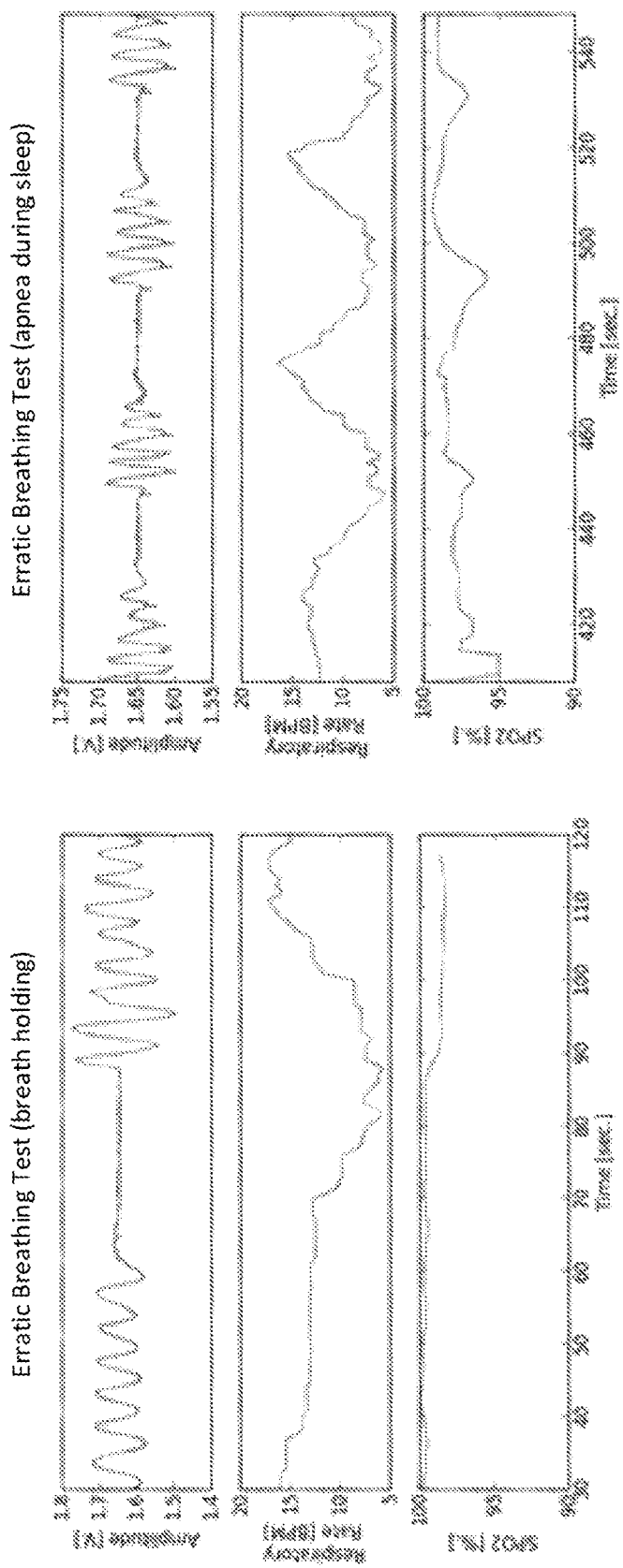
FIGS. 14A-14B depict measurements taken using a wearable device during simulated and real apnea events, according to some embodiments.

The time evolution of the indication of respiration produced by the wearable device, the RR determined therefrom, and the peripheral oxygen saturation (SpO2) measured by pulse oximetry in subject 7 of the sample group for the erratic breathing test is reported in FIG. 14A. From the respiratory signal, a plateau is found in the time interval [60,90], which corresponds to a breath hold of roughly 30 seconds. During that time frame, the respiratory rate determined based on the indication of respiration produced by the wearable device reached 5 BPM only 15 seconds after respiratory flow was held. The SpO2 was above 98% during the entire time frame analyzed.

During the spontaneous breathing study of subject 6, sleep apnea events were captured both by the wearable device and by visual counting when the patient fell asleep. The indication of respiration produced by the wearable device, the RR determined therefrom, and the peripheral oxygen saturation (SpO2) measured by pulse oximetry for subject 6 is reported in FIG. 14B. Three apnea events are recognized from the respiratory signal, where plateaus are clearly identified. The RR determined based on the indication of respiration produced by the wearable device decreased to 6 BPM during the three apnea events identified. The SpO2 was above 95% during the whole duration of the study, but some oscillations were observed, which are temporally correlated to RR determined based on the indication of respiration produced by the wearable device.

Figure 15:
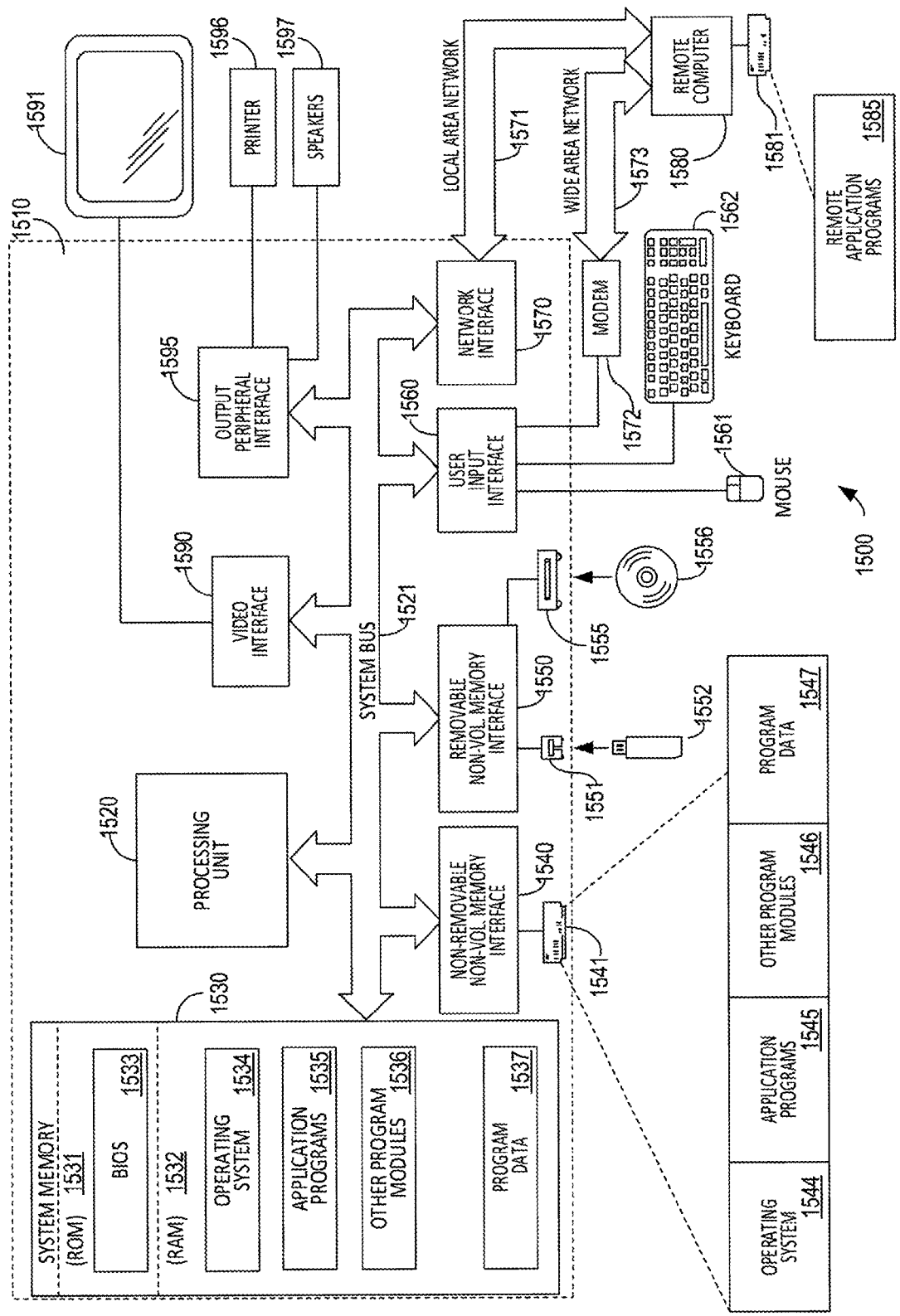
FIG. 15 illustrates an example of a computing system environment on which aspects of the invention may be implemented.

FIG. 15 illustrates an example of a suitable computing system environment 1500 on which aspects of the technology described herein may be implemented. For instance, computing system 1500 may form part or all of a controller of a wearable device (e.g., controller 115 in FIG. 1, controller 215 in FIG. 2 and/or controller components 308 and/or 309 in FIGS. 3A-3E) and/or may form part or all of a computing device with which a wearable device is in communication (e.g., computing device 250 shown in FIG. 2). The computing system environment 1500 is only one example of a suitable computing environment and is not intended to suggest any limitation as to the scope of use or functionality of the technology described herein. Neither should the computing environment 1500 be interpreted as having any dependency or requirement relating to any one or combination of components illustrated in the exemplary operating environment 1500.

The technology described herein is operational with numerous other general purpose or special purpose computing system environments or configurations. Examples of well-known computing systems, environments, and/or configurations that may be suitable for use with the technology described herein include, but are not limited to, personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices, and the like.

The computing environment may execute computer-executable instructions, such as program modules. Generally, program modules include routines, programs, objects, components, data structures, etc. that perform particular tasks or implement particular abstract data types. The technology described herein may also be practiced in distributed computing environments where tasks are performed by remote processing devices that are linked through a communications network. In a distributed computing environment, program modules may be located in both local and remote computer storage media including memory storage devices.

With reference to FIG. 15, an exemplary system for implementing the technology described herein includes a general-purpose computing device in the form of a computer 1510. For instance, computer 1510 may be implemented as controller 115 or controller 215 shown in FIGS. 1 and 2, respectively, or may be implemented as computing device 250 shown in FIG. 2.

Components of computer 1510 may include, but are not limited to, a processing unit 1520, a system memory 1530, and a system bus 1521 that couples various system components including the system memory to the processing unit 1520. The system bus 1521 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

Computer 1510 typically includes a variety of computer readable media. Computer readable media can be any available media that can be accessed by computer 1510 and includes both volatile and nonvolatile media, removable and non-removable media. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can accessed by computer 1510. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media.

The system memory 1530 includes computer storage media in the form of volatile and/or nonvolatile memory such as read only memory (ROM) 1531 and random access memory (RAM) 1532. A basic input/output system 1533 (BIOS), containing the basic routines that help to transfer information between elements within computer 1510, such as during start-up, is typically stored in ROM 1531. RAM 1532 typically contains data and/or program modules that are immediately accessible to and/or presently being operated on by processing unit 1520. By way of example, and not limitation, FIG. 15 illustrates operating system 1534, application programs 1535, other program modules 1536, and program data 1537.

The computer 1510 may also include other removable/non-removable, volatile/nonvolatile computer storage media. By way of example only, FIG. 15 illustrates a hard disk drive 1541 that reads from or writes to non-removable, nonvolatile magnetic media, a flash drive 1551 that reads from or writes to a removable, nonvolatile memory 1552 such as flash memory, and an optical disk drive 1555 that reads from or writes to a removable, nonvolatile optical disk 1556 such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 1541 is typically connected to the system bus 1521 through a non-removable memory interface such as interface 1540, and magnetic disk drive 1551 and optical disk drive 1555 are typically connected to the system bus 1521 by a removable memory interface, such as interface 1550.

The drives and their associated computer storage media discussed above and illustrated in FIG. 15, provide storage of computer readable instructions, data structures, program modules and other data for the computer 1510. In FIG. 15, for example, hard disk drive 1541 is illustrated as storing operating system 1544, application programs 1545, other program modules 1546, and program data 1547. Note that these components can either be the same as or different from operating system 1534, application programs 1535, other program modules 1536, and program data 1537. Operating system 1544, application programs 1545, other program modules 1546, and program data 1547 are given different numbers here to illustrate that, at a minimum, they are different copies. A user may enter commands and information into the computer 1510 through input devices such as a keyboard 1562 and pointing device 1561, commonly referred to as a mouse, trackball or touch pad. Other input devices (not shown) may include a microphone, joystick, game pad, satellite dish, scanner, or the like. These and other input devices are often connected to the processing unit 1520 through a user input interface 1560 that is coupled to the system bus, but may be connected by other interface and bus structures, such as a parallel port, game port or a universal serial bus (USB). A monitor 1591 or other type of display device is also connected to the system bus 1521 via an interface, such as a video interface 1590. In addition to the monitor, computers may also include other peripheral output devices such as speakers 1597 and printer 1596, which may be connected through an output peripheral interface 1595.

The computer 1510 may operate in a networked environment using logical connections to one or more remote computers, such as a remote computer 1580. The remote computer 1580 may be a personal computer, a server, a router, a network PC, a peer device or other common network node, and typically includes many or all of the elements described above relative to the computer 1510, although only a memory storage device 1581 has been illustrated in FIG. 15. The logical connections depicted in FIG. 15 include a local area network (LAN) 1571 and a wide area network (WAN) 1573, but may also include other networks. Such networking environments are commonplace in offices, enterprise-wide computer networks, intranets and the Internet.

When used in a LAN networking environment, the computer 1510 is connected to the LAN 1571 through a network interface or adapter 1570. When used in a WAN networking environment, the computer 1510 typically includes a modem 1572 or other means for establishing communications over the WAN 1573, such as the Internet. The modem 1572, which may be internal or external, may be connected to the system bus 1521 via the user input interface 1560, or other appropriate mechanism. In a networked environment, program modules depicted relative to the computer 1510, or portions thereof, may be stored in the remote memory storage device. By way of example, and not limitation, FIG. 15 illustrates remote application programs 1585 as residing on memory device 1581. It will be appreciated that the network connections shown are exemplary and other means of establishing a communications link between the computers may be used.

Having thus described several aspects of at least one embodiment of this invention, it is to be appreciated that various alterations, modifications, and improvements will readily occur to those skilled in the art.

Such alterations, modifications, and improvements are intended to be part of this disclosure, and are intended to be within the spirit and scope of the invention. Further, though advantages of the present invention are indicated, it should be appreciated that not every embodiment of the technology described herein will include every described advantage. Some embodiments may not implement any features described as advantageous herein and in some instances one or more of the described features may be implemented to achieve further embodiments. Accordingly, the foregoing description and drawings are by way of example only.

The above-described embodiments of the technology described herein can be implemented in any of numerous ways. For example, the embodiments may be implemented using hardware, software or a combination thereof. When implemented in software, the software code can be executed on any suitable processor or collection of processors, whether provided in a single computer or distributed among multiple computers. Such processors may be implemented as integrated circuits, with one or more processors in an integrated circuit component, including commercially available integrated circuit components known in the art by names such as CPU chips, GPU chips, microprocessor, microcontroller, or co-processor. Alternatively, a processor may be implemented in custom circuitry, such as an ASIC, or semicustom circuitry resulting from configuring a programmable logic device. As yet a further alternative, a processor may be a portion of a larger circuit or semiconductor device, whether commercially available, semi-custom or custom. As a specific example, some commercially available microprocessors have multiple cores such that one or a subset of those cores may constitute a processor. However, a processor may be implemented using circuitry in any suitable format.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, the invention may be embodied as a computer readable storage medium (or multiple computer readable media) (e.g., a computer memory, one or more floppy discs, compact discs (CD), optical discs, digital video disks (DVD), magnetic tapes, flash memories, circuit configurations in Field Programmable Gate Arrays or other semiconductor devices, or other tangible computer storage medium) encoded with one or more programs that, when executed on one or more computers or other processors, perform methods that implement the various embodiments of the invention discussed above. As is apparent from the foregoing examples, a computer readable storage medium may retain information for a sufficient time to provide computer-executable instructions in a non-transitory form. Such a computer readable storage medium or media can be transportable, such that the program or programs stored thereon can be loaded onto one or more different computers or other processors to implement various aspects of the present invention as discussed above. As used herein, the term "computer-readable storage medium" encompasses only a non-transitory computer-readable medium that can be considered to be a manufacture (i.e., article of manufacture) or a machine. Alternatively or additionally, the invention may be embodied as a computer readable medium other than a computer-readable storage medium, such as a propagating signal.

The terms "program" or "software," when used herein, are used in a generic sense to refer to any type of computer code or set of computer-executable instructions that can be employed to program a computer or other processor to implement various aspects of the present invention as discussed above. Additionally, it should be appreciated that according to one aspect of this embodiment, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationship between data elements.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the invention may be embodied as a method, of which examples have been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Embodiments are described herein of a wearable device that may be worn by a patient. It will be appreciated that the term "patient" is used in this context to refer generically to a subject, who need not necessarily be an admitted patient of a medical facility. Indeed, the freedom of movement offered by the techniques described herein may allow use of a wearable device at home or elsewhere. As such, the use of "patient" herein should be not seen as limiting any embodiment to use in any particular setting, such as a medical setting, nor to any particular type of individual.

In addition, embodiments of the wearable device described herein should not be seen as being limited to use in relation to a particular medical condition or in prevention of a particular medical outcome. While examples above have been given with respect to respiratory depression, for instance, it will be appreciated that the wearable device described herein could also be utilized in any situation in which it is desirable to monitor respiration of a patient, such as but not limited to during surgery, during patient recovery, in diagnosing and/or monitoring sleep apnea, etc.

Further, some actions may be described as taken by a "user." It should be appreciated that a "user" need not be a single individual, and that in some embodiments, actions attributable to a "user" may be performed by a team of individuals and/or an individual in combination with computer-assisted tools or other mechanisms.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The invention claimed is:

1. A wearable device configured to be worn between a subject's mouth and the subject's nose, the device comprising:
    a housing comprising:
        a first heat spreader arranged within the housing and comprising a first plate, the first plate at least partially exposed through an upper surface of the housing, wherein the upper surface is configured to be arranged proximate to the subject's nose when the wearable device is worn by the subject, wherein the first plate forms an uppermost surface of the housing and is configured to extend across two nostrils of the subject's nose and to absorb heat of exhaled air from both of the two nostrils, wherein the first plate is configured to be positioned between a first temperature sensor and the subject's nose;
        the first temperature sensor, wherein the first temperature sensor is thermally coupled to the first heat spreader and configured to produce a first signal indicating a first temperature reading, wherein the first temperature reading is indicative of a temperature associated with both of the two nostrils of the subject's nose;
        a second heat spreader arranged within the housing and comprising a second plate, the second plate at least partially exposed through a lower surface of the housing, wherein the lower surface is configured to be arranged proximate to the subject's mouth when the wearable device is worn by the subject, wherein the second plate is configured to be positioned between a second temperature sensor and the subject's mouth;
        the second temperature sensor, wherein the second temperature sensor is thermally coupled to the second heat spreader and configured to produce a second signal indicating a second temperature reading, distinct from the first temperature reading; and
        at least one controller coupled to the first temperature sensor and the second temperature sensor, the at least one controller configured to receive the first signal from the first temperature sensor and the second signal from the second temperature sensor, wherein the at least one controller is further configured to determine a respiration of the subject based on the received first signal indicating the first temperature reading and the received second signal indicating the second temperature reading.

2. The wearable device of claim 1, wherein at least one of the first heat spreader and the second heat spreader comprises copper.

3. The wearable device of claim 1, wherein the at least one controller is further configured to determine a respiratory rate of the subject based on the received first signal and the received second signal.

4. The wearable device of claim 3, further comprising at least one audio device configured to produce an audible indication of the respiratory rate of the subject.

5. The wearable device of claim 1, further comprising a layer of adhesive attached to the housing.

6. The wearable device of claim 1, wherein the at least one controller includes one or more processors, ASICs and/or FPGAs.

7. The wearable device of claim 1, wherein the at least one controller includes a processor and wherein the wearable device further includes a computer-readable medium storing instructions that, when executed by the processor, generates an indication of the subject's respiration based at least in part on the received first signal indicating the first temperature reading and the received second signal indicating the second temperature reading.

8. The wearable device of claim 1, further comprising at least one computer readable medium and wherein the at least one controller is configured to store a plurality of generated indications of the subject's respiration on the at least one computer readable medium.

9. The wearable device of claim 7, further comprising at least one communication device coupled to the at least one controller configured to output the generated indication of the subject's respiration to an external device.

10. A method of determining a measure of respiration of a subject, the method comprising:
    generating, by at least one controller of a wearable device worn by the subject between the subject's mouth and the subject's nose, at least one indication of the subject's respiration, wherein the wearable device comprises:
        a housing comprising:
            a first heat spreader arranged within the housing and comprising a first plate, the first plate at least partially exposed through an upper surface of the housing, wherein the upper surface is configured to be arranged proximate to the subject's nose when the wearable device is worn by the subject, wherein the first plate forms an uppermost surface of the housing and is configured to extend across two nostrils of the subject's nose and to absorb heat of exhaled air from both of the two nostrils, wherein the first plate is configured to be positioned between a first temperature sensor and the subject's nose;
            the first temperature sensor, wherein the first temperature sensor is thermally coupled to the first heat spreader and configured to produce a first signal indicating a first temperature reading, wherein the first temperature reading is indicative of a temperature associated with both of the two nostrils of the subject's nose;
            a second heat spreader arranged within the housing and comprising a second plate, the second plate at least partially exposed through a lower surface of the housing, wherein the lower surface is configured to be arranged proximate to the subject's mouth when the wearable device is worn by the subject, wherein the second plate is configured to be positioned between a second temperature sensor and the subject's mouth;
            the second temperature sensor, wherein the second temperature sensor is thermally coupled to the second heat spreader and configured to produce a second signal indicating a second temperature reading, distinct from the first temperature reading; and
            the at least one controller, wherein the at least one controller is coupled to the first temperature sensor and the second temperature sensor, and wherein the at least one controller is configured to generate the at least one indication of the subject's respiration based at least in part on the first signal indicating the first temperature reading and the second signal indicating the second temperature reading; and determining a respiratory rate, ventilation volume and/or a ventilation volume rate of the subject based at least in part on the at least one indication of the subject's respiration.

11. The method of claim 10, wherein the at least one controller of the wearable device determines the respiratory rate of the subject based at least in part on the at least one indication of the subject's respiration.

12. The method of claim 10, further comprising transmitting the at least one indication of the subject's respiration to a computing device, and wherein the computing device performs said act of determining the respiratory rate, ventilation volume and/or ventilation volume rate of the subject based at least in part on the at least one indication of the subject's respiration.

13. The method of claim 10, wherein the wearable device is attached to an upper lip of the subject via an adhesive.

14. A system comprising:
a computing device; and
a wearable device configured to be worn between a subject's mouth and the subject's nose, the device comprising:
a housing comprising:
a first heat spreader arranged within the housing and comprising a first plate, the first plate at least partially exposed through an upper surface of the housing, wherein the upper surface is configured to be arranged proximate to the subject's nose when the wearable device is worn by the subject, wherein the first plate forms an uppermost surface of the housing and is configured to extend across two nostrils of the subject's nose and to absorb heat of exhaled air from both of the two nostrils, wherein the first plate is configured to be positioned between a first temperature sensor and the subject's nose;
the first temperature sensor, wherein the first temperature sensor is thermally coupled to the first heat spreader and configured to produce a first signal indicating a first temperature reading, wherein the first temperature reading is indicative of a temperature associated with both of the two nostrils of the subject's nose;
a second heat spreader arranged within the housing and comprising a second plate, the second plate at least partially exposed through a lower surface of the housing, wherein the lower surface is configured to be arranged proximate to the subject's mouth when the wearable device is worn by the subject, wherein the second plate is configured to be positioned between a second temperature sensor and the subject's mouth;
the second temperature sensor, wherein the second temperature sensor is thermally coupled to the second heat spreader and configured to produce a second signal indicating a second temperature reading, distinct from the first temperature reading;
at least one controller coupled to the first temperature sensor and the second temperature sensor, the at least one controller configured to receive the first signal from the first temperature sensor and the second signal from the second temperature sensor, wherein the at least one controller is further configured to generate an indication of the subject's respiration based at least in part on the received first signal indicating the first temperature reading and the received second signal indicating the second temperature reading; and
a communication device configured to transmit the generated indication of the subject's respiration to the computing device.

15. The system of claim 14, wherein the computing device is configured to determine a respiratory rate of the subject based at least in part on the indication of the subject's respiration received from the communication device of the wearable device.

16. The system of claim 14, wherein at least one of the first heat spreader and the second heat spreader comprises copper.

17. The system of claim 14, wherein the wearable device further comprises a layer of adhesive attached to the housing.

18. The system of claim 14, wherein the at least one controller includes a processor and wherein the wearable device further includes a computer-readable medium storing instructions that, when executed by the processor, generates the indication of the subject's respiration based at least in part on the received first signal and the received second signal.

19. The wearable device of claim 7, wherein generating the indication of the subject's respiration based at least in part on the received first signal indicating the first temperature reading and the received second signal indicating the second temperature reading comprises:
generating a differential signal that represents a temperature difference between the first temperature reading and the second temperature reading.

20. The wearable device of claim 19, wherein generating the indication of the subject's respiration further comprises:
determining an oscillatory rate of the differential signal; and
generating the indication of the subject's respiration based on the determined oscillatory rate.

* * * * *